United States Patent
Klosterbuer et al.

(10) Patent No.: US 9,943,559 B2
(45) Date of Patent: Apr. 17, 2018

(54) NUTRITIONAL COMPOSITIONS FOR REDUCING INTESTINAL PATHOGENS

(71) Applicant: NESTEC S.A., Vevey (CH)

(72) Inventors: Abby Klosterbuer, Bloomington, MN (US); Zamzam Kabiry (Fariba) Roughead, Plymouth, MN (US)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 15/106,409

(22) PCT Filed: Dec. 19, 2014

(86) PCT No.: PCT/EP2014/078927
§ 371 (c)(1),
(2) Date: Jun. 20, 2016

(87) PCT Pub. No.: WO2015/092056
PCT Pub. Date: Jun. 25, 2015

(65) Prior Publication Data
US 2017/0000834 A1    Jan. 5, 2017

Related U.S. Application Data

(60) Provisional application No. 61/918,853, filed on Dec. 20, 2013.

(51) Int. Cl.
| | |
|---|---|
| *A61K 36/48* | (2006.01) |
| *A61K 31/733* | (2006.01) |
| *A61K 31/702* | (2006.01) |
| *A23L 29/25* | (2016.01) |
| *A23L 33/10* | (2016.01) |
| *A23L 33/22* | (2016.01) |
| *A23L 33/105* | (2016.01) |
| *A61K 9/00* | (2006.01) |
| *A61K 31/736* | (2006.01) |

(52) U.S. Cl.
CPC ............ *A61K 36/48* (2013.01); *A23L 29/25* (2016.08); *A23L 33/10* (2016.08); *A23L 33/105* (2016.08); *A23L 33/22* (2016.08); *A61K 9/0053* (2013.01); *A61K 31/702* (2013.01); *A61K 31/733* (2013.01); *A61K 31/736* (2013.01); *A23V 2002/00* (2013.01); *A61K 9/0095* (2013.01)

(58) Field of Classification Search
CPC ....... A61K 39/00; A61K 39/08; A61K 31/733; A61K 31/736
USPC ............................. 424/9.1, 9.2, 184.1, 247.1
See application file for complete search history.

(56) References Cited

U.S. PATENT DOCUMENTS

| | | | |
|---|---|---|---|
| 2004/0005305 A1 | 1/2004 | Spivey-Krobath et al. | |
| 2012/0269865 A1* | 10/2012 | Roughead ............... | A23L 1/308 424/278.1 |

FOREIGN PATENT DOCUMENTS

| | | |
|---|---|---|
| EP | 1010374 | 6/2000 |
| EP | 1175905 | 1/2002 |
| EP | 1917969 | 5/2008 |

OTHER PUBLICATIONS

Simakachorn et al. "Tolerance, Safety, and Effect on the Faecal Microbiota of an Enteral Formula Supplemented With Pre- and Probiotics in Critically Ill Children" JPGN, 2011, vol. 53, No. 2, pp. 174-181

Hoekstra et al. "Oral Rehydration Solution Containing a Mixture of Non-Digestible Carbohydrates in the Treatment of Acute Diarrhea: A Multicenter Randomized Placebo Controlled Study on Behalf of the ESPGHAN Working Group on Intestinal Infections" Journal of Pediatric Gastroenterology and Nutrition, 2004, vol. 39, pp. 239-245.

* cited by examiner

*Primary Examiner* — Rodney P Swartz
(74) *Attorney, Agent, or Firm* — K&L Gates LLP

(57) ABSTRACT

The present disclosure relates to nutritional compositions containing a fiber blend that includes soluble fibers that are fructo-oligosaccharide (FOS), acacia gum and inulin and also includes insoluble fibers that are outer pea fibers. In an embodiment, the fiber blend includes about 50% soluble fibers and about 50% insoluble fibers, and the soluble fibers are FOS in an amount of about 41% by weight of the soluble fibers, acacia gum in an amount of about 41% by weight of the soluble fibers, and inulin in an amount of about 18% by weight of the soluble fibers. In such an embodiment, the insoluble fibers are outer pea fibers. The present disclosure also relates to methods that include administering a therapeutically effective amount of a fiber blend that includes FOS, acacia gum, inulin and outer pea fibers to a patient after antibiotic treatment.

35 Claims, 36 Drawing Sheets

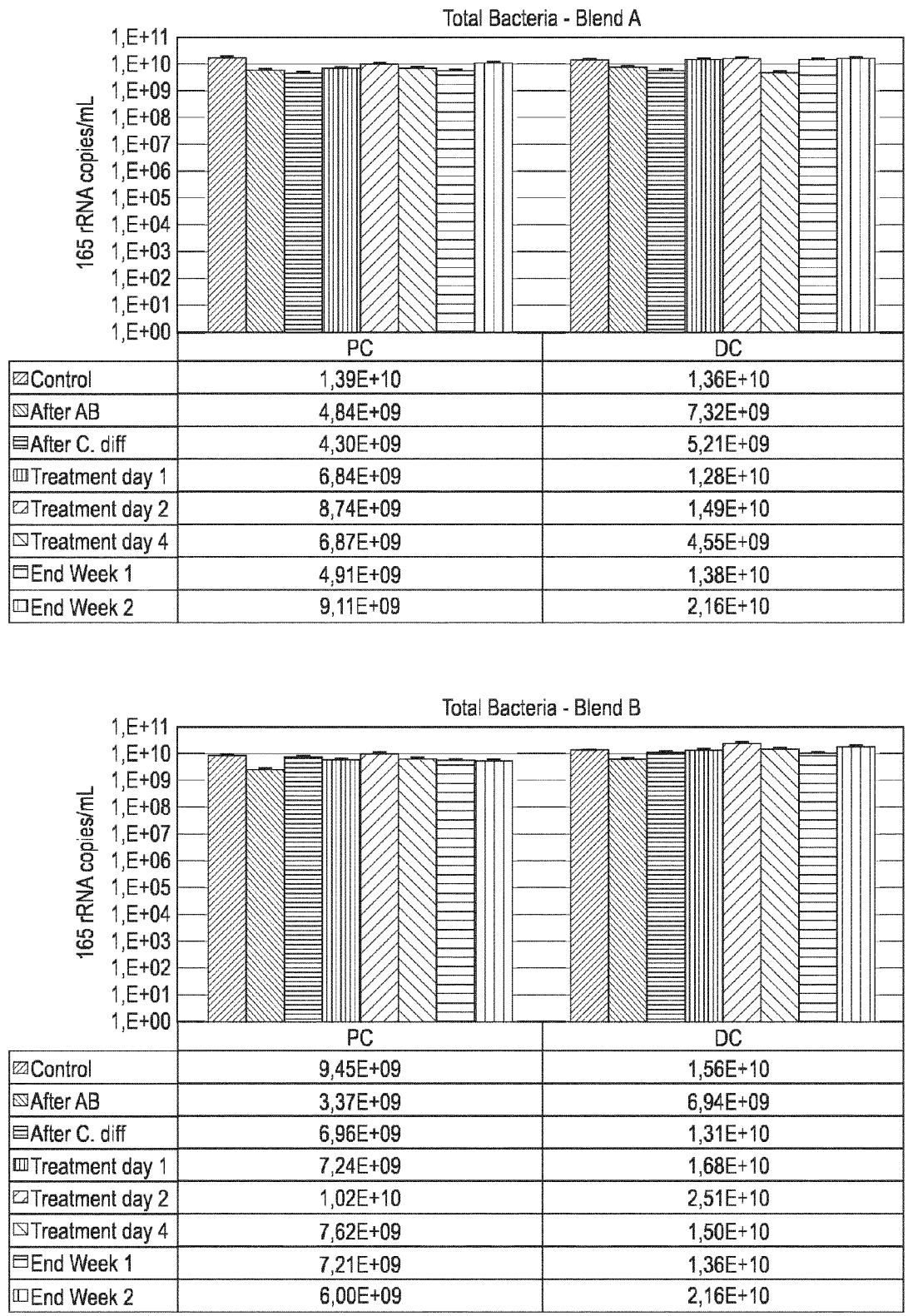
FIG. 18  Blend A = Soluble Fiber Blend
Blend B = FOS

Blend A = Soluble Fiber Blend
Blend B = FOS

Blend A = Soluble Fiber Blend
Blend B = FOS

Blend A = Soluble Fiber Blend
Blend B = FOS

Blend A = Soluble Fiber Blend
Blend B = FOS

Blend A = Soluble Fiber Blend
Blend B = FOS

Blend A = Soluble Fiber Blend
Blend B = FOS

NUTRITIONAL COMPOSITIONS FOR REDUCING INTESTINAL PATHOGENS

CROSS REFERENCE TO RELATED APPLICATIONS

The present application is a National Stage of International Application No. PCT/EP2014/078927, filed on Dec. 19, 2014, which claims priority to U.S. Provisional Patent Application No. 61/918,853, filed Dec. 20, 2013, the entire contents of which are being incorporated herein by reference.

BACKGROUND

The present disclosure is related to nutritional compositions comprising dietary fibers for reducing intestinal pathogens and also is related to methods of reducing intestinal pathogens.

Enteral feeding with standard compositions has been shown to cause adverse alterations in gut microbiota and short chain fatty acid (SCFA) production and is also associated with increased risk of *Clostridium difficile* colonization. These outcomes are also observed with overuse of antibiotics. For example, antibiotics are often administered to treat Crohn's disease, ulcerative colitis and pouchitis but can also adversely affect gut microbiota as an unintended consequence.

*C. difficile* is the leading cause of nosocomial diarrhea and is increasing in virulence and resistance to antimicrobials. Antibiotics are the primary form of treatment for *C. difficile*, and some antibiotics are effective against *C. difficile*. However, mortality from *C. difficile* infection is increasing. In addition, antibiotic treatment causes further alterations in gut microbiota and interruptions in SCFA production. For example, antibiotics inhibit bacterial growth or kill not only harmful bacteria but also populations of intestinal bacteria that are not harmful and that aid digestion of food and provide other additional health benefits.

Probiotic bacteria have been used for prevention of *C. difficile* infection, but most studies are underpowered to determine efficacy. According to the 2010 Clinical Practice Guidelines published by the Society for Healthcare Epidemiology of America (SHEA) and the Infectious Diseases Society of America (IDSA), administration of probiotic bacteria is not recommended to prevent or treat *C. difficile* infection due to limited data and potential for bloodstream infection.

The present disclosure advantageously restores microbiota balance, unlike antibiotic treatment which further disrupts the microbiota. In addition, fiber blends as disclosed herein do not increase the risk of bloodstream infection, which is a concern with probiotics.

SUMMARY

The present disclosure provides a fiber blend comprising fructo-oligosaccharide (FOS), acacia gum ("AG") and inulin, for use in the treatment or prevention of *C. difficile* infection. The fiber blend may be administered enterally for patients in need of tube feeding. Oral administration is also possible.

The soluble fibers in the blend provide a fermentable food source for colonic bacteria to maintain the normal microbial community and SCFA production, which prevents growth of opportunistic pathogens. There was no previous evidence that such blends have anti-pathogenic activity against *Clostridium difficile* or any other pathogens.

The fiber blend disclosed herein improves recovery of *Lactobacilli* concentrations, SCFAs and lactate production following antibiotic treatment and infection with the pathogen *C. difficile* in vitro. The fiber blends also improve recovery of *Bifidobacteria*, Bacteroidetes, Firmicutes, and total bacteria concentrations, as well as colonic acidification following antibiotic treatment and infection with *C. difficile* in vitro. In addition, the fiber blends result in faster washout of *C. difficile* compared to control following antibiotic treatment and infection with *C. difficile* in vitro. Specifically, the fiber blend caused faster elimination of *C. difficile* from the simulated colon.

In an embodiment, a method is provided for the treatment or prevention of a *C. difficile* infection. The method includes the steps of: administering to a patient a therapeutically effective amount of a fiber blend comprising fructo-oligosaccharides (FOS), acacia gum and inulin. In embodiments the fiber blend is administered to a patient that has a *C. difficile* infection and that has received an antibiotic treatment, after administration of the antibiotic treatment. In other embodiments the fiber blend is administered to a patient that is receiving an antibiotic treatment. In other embodiments the fiber blend is administered to a patient, followed by administering to the patient an antibiotic treatment.

In a preferred embodiment the fiber blend is administered to a patient that has a *C. difficile* infection and that has received an antibiotic treatment, after administration of the antibiotic treatment.

In an embodiment, a method is provided for the prevention or treatment of a *C. difficile* infection. The method includes the steps of: administering to a patient a nutritional composition, the composition containing a therapeutically effective amount of a fiber blend comprising fructo-oligosaccharides (FOS), acacia gum, inulin and outer pea fibers. In embodiments the nutritional composition is to be administered to a patient that has received an antibiotic treatment, after the antibiotic treatment. In other embodiments the nutritional composition is administered to a patient that is receiving an antibiotic treatment. In other embodiments the nutritional composition is administered to a patient, followed by administering to the patient an antibiotic treatment.

In an embodiment, a method is provided. The method includes the steps of: administering to a patient that received an antibiotic treatment and has a *C. difficile* infection a nutritional composition after the antibiotic treatment, the composition containing a therapeutically effective amount of a fiber blend comprising fructo-oligosaccharides (FOS), acacia gum and inulin.

In an embodiment, the FOS, the acacia gum and the inulin are the only soluble fibers in the nutritional composition.

In an embodiment, the FOS, the acacia gum and the inulin are the only fibers in the nutritional composition.

In an embodiment the fiber blend comprises fructo-oligosaccharides (FOS), acacia gum, inulin and outer pea fibers.

In an embodiment, the FOS, the acacia gum, the inulin and the outer pea fibers are the only fibers in the nutritional composition.

In an embodiment, the nutritional composition is administered enterally.

In an embodiment, the composition is administered orally.

In an embodiment, the nutritional composition is administered to the patient at least daily for at least one week after the antibiotic treatment.

In an embodiment, probiotics are not administered to the patient during the at least one week.

In an embodiment, the patient does not receive another antibiotic treatment during the at least one week.

In another embodiment, a method is provided, and the method includes the steps of: administering to a patient that has a *C. difficile* infection a nutritional composition, the composition containing a therapeutically effective amount of a fiber blend comprising fructo-oligosaccharides (FOS), acacia gum and inulin; wherein the nutritional composition is administered in conjunction with an antibiotic treatment.

In another embodiment, a method is provided, and the method includes the steps of: administering to a patient that has a *C. difficile* infection a nutritional composition, the composition containing a therapeutically effective amount of a fiber blend comprising fructo-oligosaccharides (FOS), acacia gum and inulin; and, after the patient has received the nutritional composition, administering to the patient an antibiotic treatment.

In an embodiment the fiber blend comprises fructo-oligosaccharides (FOS), acacia gum, inulin and outer pea fibers In an embodiment, the nutritional composition is administered to the patient at least daily for at least one week before the antibiotic treatment.

In an embodiment, probiotics are not administered to the patient during the at least one week.

In an embodiment, the patient does not receive another antibiotic treatment during the at least one week.

In another embodiment, a method is provided, and the method includes the steps of: administering to a patient that received an antibiotic treatment a nutritional composition at least daily for at least one week after the antibiotic treatment, the composition containing a therapeutically effective amount of a fiber blend comprising fructo-oligosaccharides (FOS), acacia gum and inulin.

In another embodiment, a method is provided, and the method includes the steps of: administering to a patient that received an antibiotic treatment a nutritional composition after the antibiotic treatment to prevent a *C. difficile* infection, the composition containing a therapeutically effective amount of a fiber blend comprising fructo-oligosaccharides (FOS), acacia gum and inulin.

In another embodiment, a method is provided, and the method includes the steps of: administering to a patient that received an antibiotic treatment and has a *C. difficile* infection a nutritional composition after the antibiotic treatment to treat the *C. difficile* infection, the composition containing a therapeutically effective amount of a fiber blend comprising fructo-oligosaccharides (FOS), acacia gum and inulin.

In another embodiment, a method is provided, and the method includes the steps of: administering to a patient who will receive an antibiotic treatment a nutritional composition before the antibiotic treatment to prevent a *C. difficile* infection, the composition containing a therapeutically effective amount of a fiber blend comprising fructo-oligosaccharides (FOS), acacia gum and inulin.

In another embodiment, a method is provided, and the method includes the steps of: administering to a patient that received an antibiotic treatment and has a *C. difficile* infection a nutritional composition, after the antibiotic treatment, to improve recovery of *Lactobacilli* concentration, the composition containing a therapeutically effective amount of a fiber blend comprising fructo-oligosaccharides (FOS), acacia gum and inulin.

In another embodiment, a method is provided, and the method includes the steps of: administering to a patient that received an antibiotic treatment and has a *C. difficile* infection a nutritional composition, after the antibiotic treatment, to improve recovery of short chain fatty acid (SCFA) production, the composition containing a therapeutically effective amount of a fiber blend comprising fructo-oligosaccharides (FOS), acacia gum and inulin.

In another embodiment, a method is provided, and the method includes the steps of: administering to a patient that received an antibiotic treatment and has a *C. difficile* infection a nutritional composition, after the antibiotic treatment, to improve recovery of lactate production, the composition containing a therapeutically effective amount of a fiber blend comprising fructo-oligosaccharides (FOS), acacia gum and inulin.

In another embodiment, a method is provided, and the method includes the steps of: administering to a patient that received an antibiotic treatment and has a *C. difficile* infection a nutritional composition, after the antibiotic treatment, to improve recovery of *Bifidobacteria* concentration, the composition containing a therapeutically effective amount of a fiber blend comprising fructo-oligosaccharides (FOS), acacia gum and inulin.

In another embodiment, a method is provided, and the method includes the steps of: administering to a patient that received an antibiotic treatment and has a *C. difficile* infection a nutritional composition, after the antibiotic treatment, to improve recovery of Bacteriodetes concentration, the composition containing a therapeutically effective amount of a fiber blend comprising fructo-oligosaccharides (FOS), acacia gum and inulin.

In another embodiment, a method is provided, and the method includes the steps of: administering to a patient that received an antibiotic treatment and has a *C. difficile* infection a nutritional composition, after the antibiotic treatment, to improve recovery of Firmicutes concentration, the composition containing a therapeutically effective amount of a fiber blend comprising fructo-oligosaccharides (FOS), acacia gum and inulin.

In another embodiment, a method is provided, and the method includes the steps of: administering to a patient that received an antibiotic treatment and has a *C. difficile* infection a nutritional composition, after the antibiotic treatment, to improve recovery of total bacteria concentration, the composition containing a therapeutically effective amount of a fiber blend comprising fructo-oligosaccharides (FOS), acacia gum and inulin.

In another embodiment, a method is provided, and the method includes the steps of: administering to a patient that received an antibiotic treatment and has a *C. difficile* infection a nutritional composition, after the antibiotic treatment, to improve colonic acidification, the composition containing a therapeutically effective amount of a fiber blend comprising fructo-oligosaccharides (FOS), acacia gum and inulin.

In another embodiment, a method is provided, and the method includes the steps of: administering to a patient that received an antibiotic treatment and has a *C. difficile* infection a nutritional composition, after the antibiotic treatment, to improve elimination of *C. difficile* from the colon, the composition containing a therapeutically effective amount of a fiber blend comprising fructo-oligosaccharides (FOS), acacia gum and inulin.

In another embodiment, a method is provided, and the method includes the steps of: administering to a patient that received an antibiotic treatment and has a *C. difficile* infection a nutritional composition, after the antibiotic treatment, to decrease the concentration of *C. difficile* in the colon, the composition containing a therapeutically effective amount of a fiber blend comprising fructo-oligosaccharides (FOS), acacia gum and inulin.

In an alternative embodiment the fiber blend is administered to a patient before the patient receives an antibiotic treatment.

In a further alternative embodiment the fiber blend is administered to a patient in conjunction with administering to the patient an antibiotic treatment.

In an embodiment the fiber blend further comprises an insoluble fiber wherein the insoluble fiber is selected from a soy fiber, an outer pea fiber or a combination thereof. In a preferred embodiment the fiber blend comprises fructo-oligosaccharides (FOS), acacia gum, inulin and outer pea fibers.

In an embodiment the fiber blend comprises a further soluble fiber, for example partially hydrolyzed guar gum ("PHGG"). For example, PHGG may be provided in an amount of up to 10 g/L, such as in an amount from about 2 g/L to about 9 g/L. In an embodiment the fiber blend comprises fructo-oligosaccharides (FOS), acacia gum, inulin and PHGG.

The present disclosure provides a fiber blend comprising fructo-oligosaccharide (FOS), acacia gum ("AG"), and inulin for use in the treatment or prevention of *C. difficile* infection.

In a preferred embodiment the present disclosure provides a fiber blend comprising fructo-oligosaccharide (FOS), acacia gum ("AG") and inulin for use in the treatment or prevention of *C. difficile* infection in a patient that has received an antibiotic treatment prior to administration of the fiber blend.

In an alternative embodiment the present disclosure provides a fiber blend comprising fructo-oligosaccharide (FOS), acacia gum ("AG") and inulin for use in the treatment or prevention of *C. difficile* infection in a patient that receives an antibiotic treatment in conjunction with the fiber blend, or in a patient that will receive an antibiotic treatment subsequent to administration of the fiber blend.

The present disclosure provides a fiber blend comprising fructo-oligosaccharide (FOS) in an amount of about 38% to 44% by weight of the blend, acacia gum ("AG") in an amount of about 38% to about 44% by weight of the blend, inulin is present in an amount of about 12% to about 24% by weight of the blend, for use in the treatment or prevention of *C. difficile* infection. The fiber blend may be administered enterally for patients in need of tube feeding. Oral administration is also possible.

In an embodiment the fiber blend comprises a further soluble fiber, for example partially hydrolyzed guar gum ("PHGG"). For example, PHGG may be provided in an amount of up to 10 g/L, such as in an amount from about 2 g/L to about 9 g/L. In an embodiment the fiber blend comprises fructo-oligosaccharides (FOS), acacia gum, inulin and PHGG.

In an embodiment the fiber blend further comprises an insoluble fiber wherein the insoluble fiber is selected from a soy fiber, an outer pea fiber or a combination thereof. In a preferred embodiment the fiber blend comprises fructo-oligosaccharides (FOS), acacia gum, inulin and outer pea fibers.

The present disclosure provides a fiber blend having about 50% soluble fibers and about 50% insoluble fibers by weight of the blend. The soluble fibers comprise about 41% fructo-oligosaccharide (FOS), about 41% acacia gum, and about 18% inulin by weight of the blend, for use in the treatment or prevention of *C. difficile* infection. The insoluble fibers are outer pea fibers. The fiber blend may be administered enterally for patients in need of tube feeding. Oral administration is also possible.

In an embodiment there is provided a fiber blend comprising fructo-oligosaccharide (FOS), acacia gum ("AG") and inulin for use to improve recovery of *Lactobacilli* concentration, improve recovery of short chain fatty acid (SCFA) production, and/or improve recovery of lactate production, in a patient that has received an antibiotic treatment and has a *C. difficile* infection.

In an embodiment there is provided a fiber blend comprising fructo-oligosaccharide (FOS), acacia gum ("AG") and inulin for use to improve recovery of *Bifidobacteria* concentration, to improve recovery of Bacteriodetes concentration, to improve recovery of Firmicutes concentration, to improve recovery of total bacteria concentration, to improve colonic acidification, and/or to improve elimination of *C. difficile* from the colon, and/or reduce concentration of *C. difficile* in the colon, in a patient that has received an antibiotic treatment and has a *C. difficile* infection.

In an alternative embodiment the fiber blend is formulated for use in a patient that has a *C. difficile* infection before the patient receives an antibiotic treatment.

In a further alternative embodiment the fiber blend is formulated for administration in conjunction with antibiotic treatment to a patient that has a *C. difficile* infection.

In another embodiment there is provided a nutritional composition for use in the prevention or treatment of *C. difficile* infection. The nutritional composition includes fructo-oligosaccharide (FOS), acacia gum ("AG") and inulin. In a particular embodiment the nutritional composition comprises a fiber blend that is about 50% soluble fibers and about 50% insoluble fibers; the soluble fibers are fructo-oligosaccharide (FOS) in an amount of about 41% by weight of the soluble fibers, acacia gum in an amount of about 41% by weight of the soluble fibers, and inulin in an amount of about 18% by weight of the soluble fibers; the insoluble fibers are outer pea fibers; and the composition is designed to be administered to an individual by at least one of oral or enteral administration.

In an embodiment, the fiber blend is the only fiber in the composition.

Additional features and advantages are described herein and will be apparent from the following Detailed Description and the figures.

DETAILED DESCRIPTION

Definitions

Figure 1:
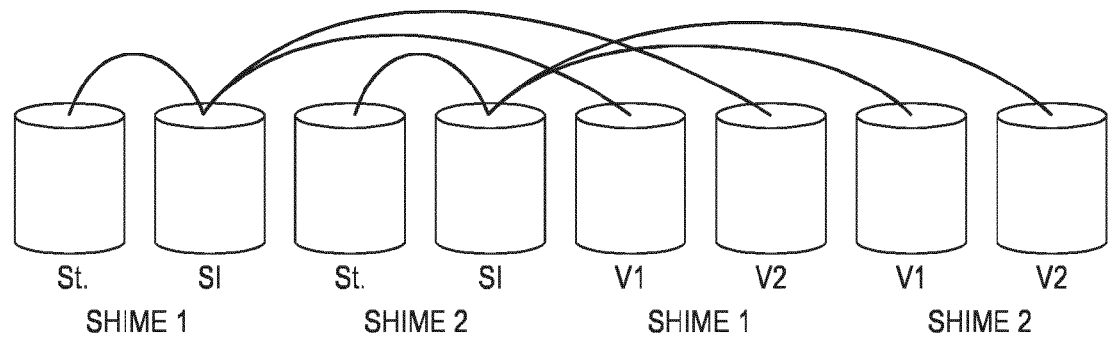
FIG. 1 shows an adapted Simulator of the Human Intestinal Microbial Ecosystem ("SHIME") system which includes sequential reactors that simulate the stomach, the duodenum and the ascending colon, and two SHIME systems are configured in parallel ("TWINSHIME") to attain identical environmental conditions for both systems.

All dosage ranges contained within this application are intended to include all numbers, whole or fractions, contained within said range. All percentages expressed herein are by weight of the total weight of the fiber blend unless expressed otherwise. As used herein, "about" is understood to refer to numbers in a range of numerals. Moreover, all numerical ranges herein should be understood to include all integer, whole or fractions, within the range.

As used in this disclosure and the appended claims, the singular forms "a," "an" and "the" include plural referents unless the context clearly dictates otherwise. Thus, for example, reference to "an amino acid" includes a mixture of two or more amino acids, and the like.

As used herein, "animal" includes, but is not limited to, mammals, which includes but is not limited to, rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage. As used herein, the term "patient" is understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human, having or at risk for a medical condition that can benefit from the treatment.

"Nutritional compositions," as used herein, are understood to include any number of optional additional ingredients, including conventional food additives, for example one or more, acidulants, additional thickeners, buffers or agents for pH adjustment, chelating agents, colorants, emulsifiers, excipient, flavor agent, mineral, osmotic agents, a pharmaceutically acceptable carrier, preservatives, stabilizers, sugar, sweeteners, texturizers, and/or vitamins. The optional ingredients can be added in any suitable amount.

As used herein, "therapeutically effective amount" is an amount that prevents a deficiency, treats a disease or medical condition in an individual or, more generally, reduces symptoms, manages progression of the diseases or provides a nutritional, physiological, or medical benefit to the individual. A treatment can be patient- or doctor-related.

As used herein, the terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition, such as nitrogen imbalance or muscle loss. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition.

As used herein, a "tube feed" is a complete or incomplete nutritional product or composition that is administered to an animal's gastrointestinal system, other than through oral administration, including but not limited to a nasogastric tube, an orogastric tube, a gastric tube, a jejunostomy tube ("J-tube"), percutaneous endoscopic gastrostomy ("PEG"), and a port, such as a chest wall port that provides access to the stomach, jejunum and other suitable access ports.

The term "microorganism" is meant to include bacterium, yeast and/or fungi, a cell growth medium with a microorganism, or a cell growth medium in which a microorganism was cultivated.

Exemplary Embodiments

Enteral nutrition is the preferred method of nutrient delivery for individuals who are unable to meet their nutritional needs orally. A standard formula is most commonly used in individuals with no specific medical concerns. These formulas have macro- and micronutrient contents which meet the recommendations for a healthy population and are generally well tolerated. In the past, fiber-free enteral formulas were preferred due to problems with tube clogging, as well as the notion that bowel rest was beneficial. As clogging problems due to fiber have since been mostly eliminated, it is now recognized that fiber can be included in such formulations in order to exert a number of beneficial physiological effects that are desirable for this population.

Accordingly, the nutritional composition contains a fiber blend comprising soluble fibers that include fructo-oligosaccharide (FOS), acacia gum and inulin, In a preferred embodiment the nutritional composition contains the soluble fibers comprising fructo-oligosaccharide (FOS), acacia gum and inulin in an amount of from about 0.5 g to about 25 g of per litre of the nutritional composition, preferably from about 1.0 g to about 20 g per litre of the nutritional composition, more preferably from about 1.5 g to about 15 g per litre of the nutritional composition. In a particular embodiment the nutritional composition contains the soluble fibers comprising fructo-oligosaccharide (FOS), acacia gum and inulin in an amount of about 6 g to about 15 g per litre of the nutritional composition, preferably from about 6 g to about 13 g per litre of the nutritional composition. In a particular embodiment the nutritional composition contains the soluble fibers comprising fructo-oligosaccharide (FOS), acacia gum and inulin in an amount of about 6.5 g per litre of the nutritional composition.

In an embodiment the fiber blend further comprises insoluble fibers that include outer pea fibers. In a preferred embodiment, the fiber blend comprises the soluble fibers and the insoluble fibers in a ratio soluble fibers:insoluble fibers of about 40:60 to about 60:40. In a particular embodiment, the fiber blend is about 50% soluble fibers and about 50% insoluble fibers. In a preferred embodiment the nutritional composition contains the fiber blend comprising fructo-oligosaccharide (FOS), acacia gum, inulin, and outer pea fibers in an amount of from about 3 g to about 30 g of per litre of the nutritional composition, preferably from about 5 g to about 25 g per litre of the nutritional composition, more preferably from about 5 g to about 20 g per litre of the nutritional composition. In a particular embodiment the nutritional composition contains the blend soluble fibers comprising fructo-oligosaccharide (FOS), acacia gum and inulin in an amount of about 10 g to about 20 g per litre of the nutritional composition. In another particular embodiment the nutritional composition contains the blend soluble fibers comprising fructo-oligosaccharide (FOS), acacia gum and inulin in an amount of about 5 g to about 9 g per litre of the nutritional composition.

The soluble fibers provide a fermentable food source for colonic bacteria, which helps maintain the normal microbial community and SCFA production to prevent growth of opportunistic pathogens. The insoluble fibers provide benefits of regularity and fecal bulking.

Preferably, the fiber blend is the only fiber in the nutritional composition. For example, FOS, acacia gum and inulin can be the only fibers in the composition. In another embodiment FOS, acacia gum and inulin can be the only soluble fibers in the composition, and outer pea fibers can be the only insoluble fibers in the composition.

In another embodiment the fiber blend can comprises a further soluble fiber, for example partially hydrolyzed guar gum ("PHGG"). For example, PHGG may be provided in an amount of up to 10 g/L, such as in an amount from about 2 g/L to about 9 g/L. In an embodiment the fiber blend comprises fructo-oligosaccharides (FOS), acacia gum, inulin and PHGG. In an embodiment fructo-oligosaccharides (FOS), acacia gum, inulin and PHGG can be the only fibers in the composition.

The FOS provides short chain fibers, the inulin provides medium chain fibers, and the acacia gum provides long chain fibers. Thus the fiber blend provides fibers fermented at different rates thereby conferring benefits along the entire length of the colon.

In a preferred embodiment, the nutritional composition comprises FOS in an amount of about 35 to about 44% by weight; acacia gum in an amount of about 38% to about 50% by weight; and inulin in an amount of 12 to 24% by weight In a more preferred embodiment, the nutritional composition of the present disclosure comprises FOS and the acacia gum each present in an amount of about 40% to about 42% by weight; and inulin present in an amount of about 16% to about 20% by weight.

It is advantageous for the FOS and the acacia gum to be present in a weight ratio of about 44:38 to about 35:50, or about 42:40 to about 40:42, or about 1:1. Also, it is advantageous for the FOS and inulin to be present in a weight ratio of about 38:24 to about 44:12, or about 40:20 to about 42:16, or about 7:3.

In a preferred embodiment, the soluble fibers are FOS in an amount of about 41% by weight of the soluble fibers; acacia gum in an amount of about 41% by weight of the soluble fibers; and inulin in an amount of about 18% by weight of the soluble fibers.

FOS and inulin are low-viscosity soluble fibers that are linear fructans containing β(2-1) fructosyl-fructose glycosidic bonds. FOS are short chain polymers of simple carbohydrates, and the polymers do not behave like simple sugars in the body. FOS occur naturally in chicory, bananas, garlic, and certain other foods, and are, technically, a soluble fiber. Inulin refers to molecules with an average degree of polymerization greater than or equal to 10, and FOS has a degree of polymerization less than 10 and can be obtained as a hydrolysis product of inulin or by synthesis from fructose or fructose and glucose.

Acacia gum is a natural, non-viscous and soluble fiber belonging to the complex arabinogalactan family. Acacia gum is a highly branched, high molecular weight molecule comprised of galactose, arabinose, rhamnose, and glucuronic acid units. This native substance has an average molecular weight between 300 and 800 kDa. Acacia gum is composed of three different fractions, namely 1% glycoprotein, 1-10% arabinogalactan-protein, and 90-99% arabinogalactan. Acacia gum is slowly fermented compared to other soluble fibers and increases production of SCFA, and therefore may benefit the distal colon.

The insoluble fibers comprise outer pea fibers and preferably consist of outer pea fibers. Outer pea fiber is obtained from pea hulls and is primarily composed of arabinose-rich hemicelluloses, cellulose, and pectic substances, such as uronic acid. Acacia gum can assist in maintaining formulation viscosity when outer pea fibers are present.

The nutritional composition may be prepared in liquid form. Water is the most common carrier for the components of the composition, but the composition can be provided in other liquids such as, for example, milk, fruit juice, coffee, tea or other beverages, when such compositions are orally administered. Water is typically used for enteral formulations.

The nutritional composition can be a dry powdered formulation. The powdered formulation can be made by combining dry powdered ingredients or can be made from a liquid nutritional composition by drying the liquid composition with one of the processes known in the art, including spray drying, freeze drying or other drying techniques, to produce a dry powdered composition. If desired, other nutritional components or compositions can be added to the liquid prior to drying to provide enhanced nutritional benefits to the powdered formulation. Such powdered formulations have a much greater shelf life and can be packaged for storage and transport for future use. At that time, the powdered formulations can be reconstituted with water or other fluids and then administered to the individual orally or enterally. The powdered formulation can be packaged in various containers, including those for bulk provision of such powdered formulations for adding to a liquid in a glass, bottle or other fluid containing vessel, or a single serving can be provided with the powder present in a container to which water or other fluids can be added to form the liquid for oral or enteral administration.

In an embodiment, the nutritional composition is a complete nutrition product that contains sufficient types and levels of macronutrients (protein, fats and carbohydrates) and micronutrients to be sufficient as a sole source of nutrition for the animal to which the composition is administered. In another embodiment, the nutritional composition is an incomplete nutrition product that does not contain sufficient levels of macronutrients (protein, fats and carbohydrates) or micronutrients to be sufficient as a sole source of nutrition for the animal to which the composition is administered.

In a preferred embodiment, the nutritional composition does not include a microorganism. In such embodiments, the nutritional composition does not include probiotics. Probiotics are food-grade microorganisms, metabolites, microbial cell preparations or components of microbial cells that can confer health benefits on the host when administered in adequate amounts, more specifically, that beneficially affect a host by improving its intestinal microbial balance, leading to effects on the health or well-being of the host. See Salminen S., Ouwehand A., Benno Y. et al., "Probiotics: how should they be defined?" *Trends Food Sci. Technol.*, 1999: 10, 107-10. In general, it is believed that these microorganisms inhibit or influence the growth and/or metabolism of pathogenic bacteria in the intestinal tract and may also activate the immune function of the host. Non-limiting examples of probiotics include *Aerococcus, Aspergillus, Bacillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella* and combinations thereof.

In an embodiment, the nutritional composition comprises protein in addition to the fiber blend. Non-limiting examples of suitable proteins include dairy-based proteins, plant-based proteins, animal-based proteins and artificial proteins. Dairy-based proteins include, for example, casein, caseinates (e.g., all forms including sodium, calcium, potassium caseinates), casein hydrolysates, whey (e.g., all forms including concentrate, isolate, demineralized), whey hydrolysates, milk protein concentrate, and milk protein isolate. Plant-based proteins include, for example, soy protein (e.g., all forms including concentrate and isolate), pea protein (e.g., all forms including concentrate and isolate), canola protein (e.g., all forms including concentrate and isolate), other plant proteins that commercially are wheat and fractionated wheat proteins, corn and corn fractions including zein, rice, oat, potato, peanut, green pea powder, green bean powder, and any proteins derived from beans, lentils, and pulses.

In an embodiment, the nutritional composition further comprises fats, such as, for example, fish oils or nonmarine oils, in addition to the fiber blend. Non-limiting examples of fish oils include docosahexaenoic acid ("DHA") and eicosapentaenoic acid ("EPA"). Alternatively or additionally, DHA and EPA may be present from a non-fish oil source, e.g., algae, modified plants, and the like. In an embodiment, the nutritional composition further comprises DHA, EPA or a combination thereof in addition to the fiber blend.

In some embodiments, the nutritional composition further comprises antioxidants in addition to the fiber blend. Non-limiting examples of suitable antioxidants include substances that inhibit oxidation or reactions promoted by Reactive Oxygen Species ("ROS") and other radical and non-radical species and also include molecules capable of slowing or preventing the oxidation of other molecules. For example, in addition to the fiber blend, the nutritional composition can further comprise carotenoids, coenzyme Q10 ("CoQ10"), flavonoids, glutathione Goji (wolfberry), hesperidine, lactowolfberry, lignan, lutein, lycopene, polyphenols, selenium, vitamin A, vitamin $B_1$, vitamin $B_6$, vitamin $B_{12}$, vitamin C, vitamin D, vitamin E, zeaxanthin, or combinations thereof.

In some embodiments, the nutritional composition further comprises vitamins, minerals or combinations thereof in addition to the fiber blend. Vitamins include fat-soluble or water-soluble organic substances essential in minute amounts for normal growth and activity of the body. The vitamins used in the composition are obtained naturally from plant and animal foods or synthetically made and can include pro-vitamins, derivatives and analogs. Non-limiting examples of suitable vitamins include Vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin in vitamin supplements), Vitamin C, Vitamin D, Vitamin E, Vitamin K, folic acid, biotin and combinations thereof. Non-limiting examples of suitable minerals include boron, calcium, chromium, copper, iodine, iron, magnesium, manganese, molybdenum, nickel, phosphorus, potassium, selenium, silicon, tin, vanadium, zinc and combinations thereof.

In an embodiment, the nutritional composition further comprises phytonutrients that are health-promoting compounds from plant sources. The phytonutrients that can be used in the nutritional compositions are any chemicals produced by a plant that impart one or more health benefits on the user. Non-limiting examples of suitable phytonutrients include phenolic compounds, terpenes, betalains, organosulfides, protein inhibitors, other organic acids and combinations thereof.

The nutritional composition can be used in a method that includes administering to a patient that received antibiotic treatment a therapeutically effective amount of the fiber blend after the antibiotic treatment. In another aspect, the nutritional composition can be used in a method that includes administering to a patient that received antibiotic treatment and has a *C. difficile* infection a therapeutically effective amount of the fiber blend after the antibiotic treatment.

In further aspects, the nutritional composition can be used in a method that includes the steps of administering to a patient that received antibiotic treatment a therapeutically effective amount of the fiber blend, after the antibiotic treatment, to prevent a *C. difficile* infection. The nutritional composition can also be used in a method that includes the steps of administering to a patient that received an antibiotic treatment and has a *C. difficile* infection a therapeutically effective amount of the fiber blend, after the antibiotic treatment, to treat the *C. difficile* infection.

In addition, the nutritional composition can be used in a method for treating or preventing a *C. difficile* infection that includes the steps of administering to a patient has a *C. difficile* infection, a therapeutically effective amount of the fiber blend, followed by administering to the patient antibiotic treatment.

In addition, the nutritional composition can be used in a method for treating or preventing a *C. difficile* infection that includes the steps of administering to a patient that has a *C. difficile* infection, a therapeutically effective amount of the fiber blend, or in conjunction with administering to the patient antibiotic treatment In still further aspects, the nutritional composition can be used in methods that include the steps of administering to a patient that received an antibiotic treatment and has a *C. difficile* infection a therapeutically effective amount of the fiber blend, after the antibiotic treatment, to improve recovery of *Lactobacilli* concentration, improve recovery of short chain fatty acid (SCFA) production, and/or improve recovery of lactate production. The improvements are relative to the effects obtained from a composition lacking the fiber blend.

Yet further, the nutritional composition can be used in methods that include the steps of administering to a patient that received an antibiotic treatment and has a *C. difficile* infection a therapeutically effective amount of the fiber blend, after the antibiotic treatment, to improve recovery of *Bifidobacteria* concentration, to improve recovery of Bacteriodetes concentration, to improve recovery of Firmicutes concentration, to improve recovery of total bacteria concentration, to improve colonic acidification, and/or to improve elimination of *C. difficile* from the colon/decrease concentration of *C. difficile* in the colon. The improvements are relative to the effects obtained from a composition lacking the fiber blend.

In still further aspects, the nutritional composition can be used in methods that include the steps of administering to a patient that has a *C. difficile* infection a therapeutically effective amount of the fiber blend, followed by, or in conjunction with administering to the patient an antibiotic treatment, to improve recovery of *Lactobacilli* concentration, improve recovery of short chain fatty acid (SCFA) production, and/or improve recovery of lactate production. The improvements are relative to the effects obtained from a composition lacking the fiber blend.

Yet further, the nutritional composition can be used in methods that include the steps of administering to a patient that has a *C. difficile* infection a therapeutically effective amount of the fiber blend, followed by or in conjunction administering to the patient an antibiotic treatment, to improve recovery of *Bifidobacteria* concentration, to improve recovery of Bacteriodetes concentration, to improve recovery of Firmicutes concentration, to improve recovery of total bacteria concentration, to improve colonic acidification, and/or to improve elimination of *C. difficile* from the colon. The improvements are relative to the effects obtained from a composition lacking the fiber blend.

For example, in an embodiment, the nutritional composition comprising the therapeutically effective amount of the fiber blend may be administered to the patient at least once daily from the antibiotic treatment to at least one week thereafter, preferably at least two weeks thereafter and even more preferably at least three weeks thereafter. In an embodiment, the patient is treated with the fiber blend without further antibiotics and without probiotics.

The nutritional composition can be used for long-term administration, specifically continuous administrations for more than 6 weeks, or short-term administration, specifically continuous administrations for less than 6 weeks. The nutritional composition can be used for tube-feed administration. In addition to enteral administration, oral administration is also possible.

NON-LIMITING EXAMPLES

Example 1

In Vitro Evaluation of the Fiber Blend Using the Simulator of the Human Intestinal Microbial Ecosystem ("SHIME")
Experimental Design
In vitro approaches to study the gastrointestinal tract and intestinal microbial processes offer an excellent experimental setup to study possible prebiotic properties of selected food ingredients. The application of well-designed continuous models allows the in-depth study of the biological activity of selected molecules in the gut under representative environmental conditions.

The study investigated a fiber blend of 50% soluble fibers and 50% insoluble fibers; the soluble fibers are FOS in an amount of about 41% by weight of the soluble fibers, acacia gum in an amount of about 41% by weight of the soluble fibers, and inulin in an amount of about 18% by weight of the soluble fibers, and the insoluble fibers are outer pea fibers (hereafter "the fiber blend"). To study potential properties of the fiber blend in detail using an in vitro setup, a continuous model was used, which cultures the complex intestinal microbial ecosystem under representative conditions. Moreover, as previous in vitro and in vivo studies have shown that the evaluation of prebiotic properties may only be performed after two to three weeks of continuous administration of the compound, the model should simulate repeated ingestion of the prebiotic. Therefore, the dynamic SHIME simulator of the human gastrointestinal tract was used to evaluate the efficacy of treatment with the fiber blend.

The reactor setup was adapted from the SHIME, representing the gastrointestinal tract ("GIT") of the adult human, as described by Molly et al., "Development of a 5-step multichamber reactor as a simulation of the human intestinal microbial ecosystem," *Applied Microbiology and Biotechnology*, 39:254-258 (1993). The SHIME uses reactors simulating the different parts of the human gastrointestinal tract. See, e.g., FIG. 1.

The first two reactors used the fill-and-draw principle to simulate different steps in food uptake and digestion, with peristaltic pumps adding a defined amount of SHIME feed (140 mL 3×/day) and pancreatic and bile liquid (60 mL 3×/day), respectively to the stomach ("St.") and duodenum ("SI") and emptying the respective reactors after specified intervals. The other compartments (V1, V2) were continuously stirred reactors with constant volume and pH control. Retention time and pH of vessels V1, V2 were chosen to resemble in vivo conditions of the ascending colon. Inoculum preparation, retention time, pH, temperature settings and reactor feed composition were previously described by Possemiers et al., "PCR-DGGE-based quantification of stability of the microbial community in a simulator of the human intestinal microbial ecosystem," *FAMS Microbiology Ecology*, 49:495-507 (2004). The SHIME has been extensively used for about 20 years for both scientific and industrial projects and has been validated with in vivo parameters.

As shown in FIG. 1, to evaluate the anti-pathogenic effect of the fiber blend, the pathogen *C. difficile* was added to vessels simulating the ascending colon of a TWINSHIME system in a gut-representative microbial community after an antibiotic pulse to simulate what normally occurs before an infection in a hospital. Vessel V1 contained *C. perfringens*, and vessel V2 contained *C. difficile*. Vessel V2 received a preliminary antibiotic shot with a mix of Amoxicillin, Ciprofloxacine and Tetracycline in the vessels that then were inoculated with *C. difficile*. For *C. perfringens*, no antibiotic was added and no pathogen addition was performed in vessel V1 because this opportunistic pathogen is normally present in the SHIME. The antibiotic treatment consisted of a mix of 40 ppm Amoxicillin, 40 ppm Ciprofloxacine, and 10 ppm Tetracycline.

The first objective of the study was to evaluate whether or not the fiber blend had an anti-pathogenic activity with or without antibiotic treatment. The second objective was to follow the recovery of the microbial community in composition and functionality after the antibiotic pulse and following the addition of the fiber blend.

For these experiments, a TWINSHIME setup was used by operating two systems in parallel at the same time (SHIME 1=control; SHIME 2=fiber blend treatment). Identical environmental conditions for both systems were obtained by identical pH and temperature control and by using two-headed pumps for liquid transfer between the reactors. The fiber blend was provided only to SHIME 2, and the concentration of the pathogens was measured in the ascending colon of SHIME 2 as compared to SHIME 1. This approach addressed the fact that the antimicrobial effect is not necessary related to a direct effect of the fiber blend but could be due to metabolites produced by other bacteria using the fiber blend.

Figure 2:
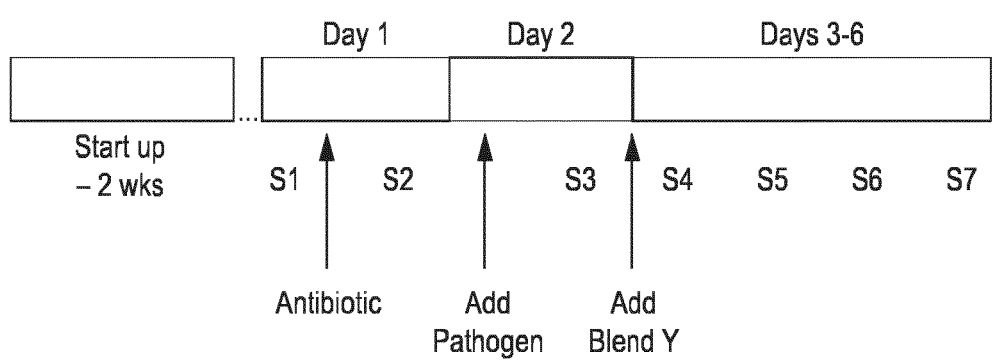
FIG. 2 is a sampling scheme for *C. difficile* (V2).

As shown in FIG. 2, the first stage of the study was a start-up stage. After inoculation of the ascending colon reactors with an appropriate fecal sample (elder donor with a low concentration of *Bifidobacteria*), a two-week start up period allowed the microbial community to differentiate in the different reactors depending on the local environmental conditions. Samples from each of the ascending colon vessels were collected daily as shown in FIG. 2 to perform the following analyses: 1) short chain fatty acid (SCFA), lactate and ammonium production; 2) ΔpH daily; 3) qPCR for *lactobacilli, Bifidobacteria*, total bacteria, bacteroidetes and firmicutes; and 4) qPCR specific for the pathogens.
Results—SCFA SCFA are the typical end products of mainly saccharolytic fermentation by the intestinal bacteria. SCFA profiles consist mainly of acetate, propionate and butyrate with small amounts of other acids such as isobutyric, valeric, isovaleric and caproic acid. Whereas acetate can be absorbed from the gut and used as an energy substrate by the host, butyrate acts as the main energy substrate for the gut epithelium and has proven protective effects against inflammation and colon cancer. Propionate has similar local activity in the gut as compared to butyrate yet is also transported to the liver where propionate was shown to have positive cholesterol-lowering effects and effects on glycemic control. For this reason, butyrate and propionate are considered more health-beneficial for the host as compared to acetate, and modulation of the microbial fermentation profiles in the gut toward increased butyrate and/or propionate production is considered beneficial.

Figure 3:
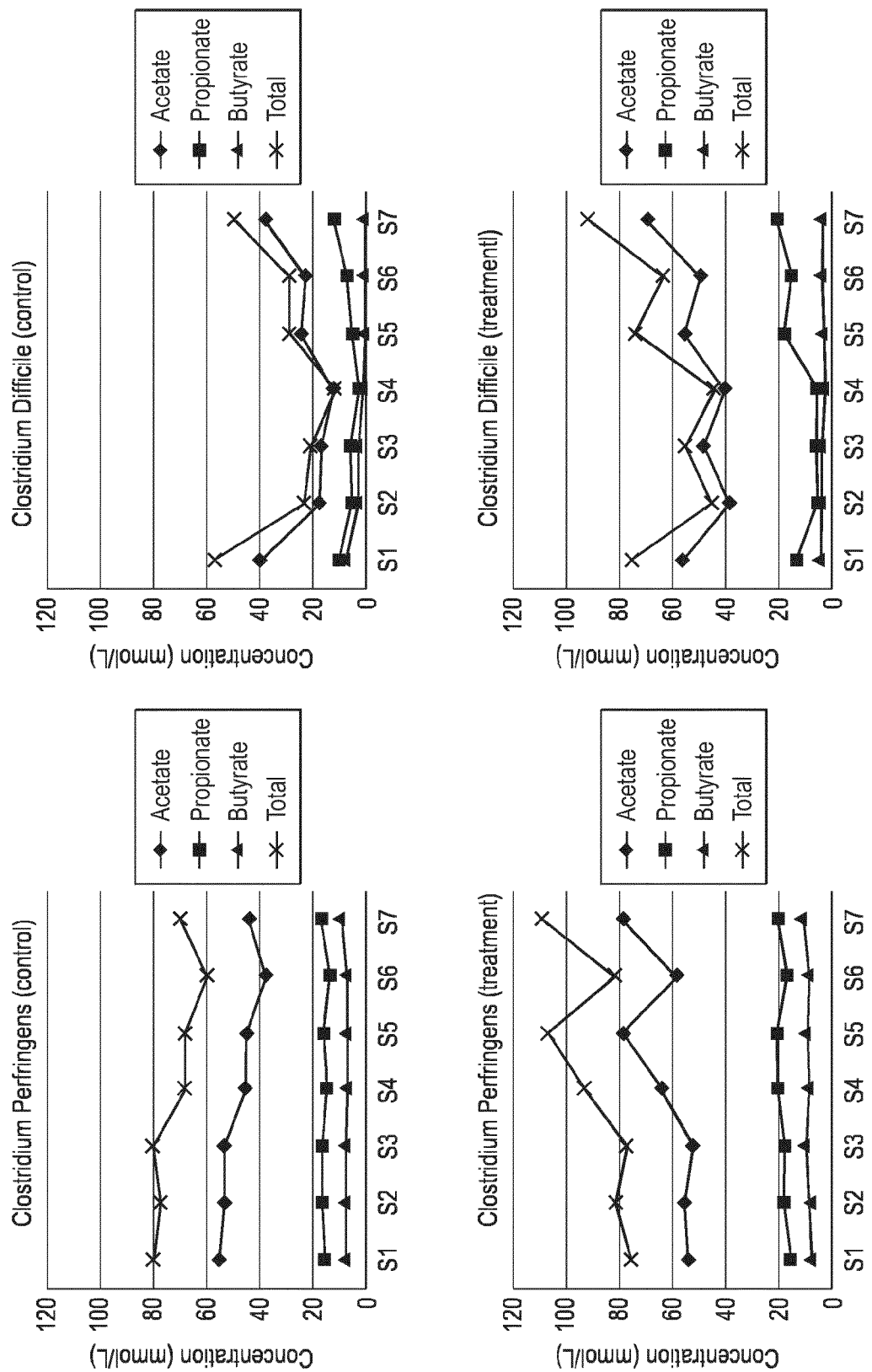
FIG. 3 shows graphs of concentrations of total SCFA, acetate, propionate and butyrate for each daily sample S1-S7 for a control SHIME and a SHIME in which the fiber blend was used for each of V1 and V2.
Figure 4:
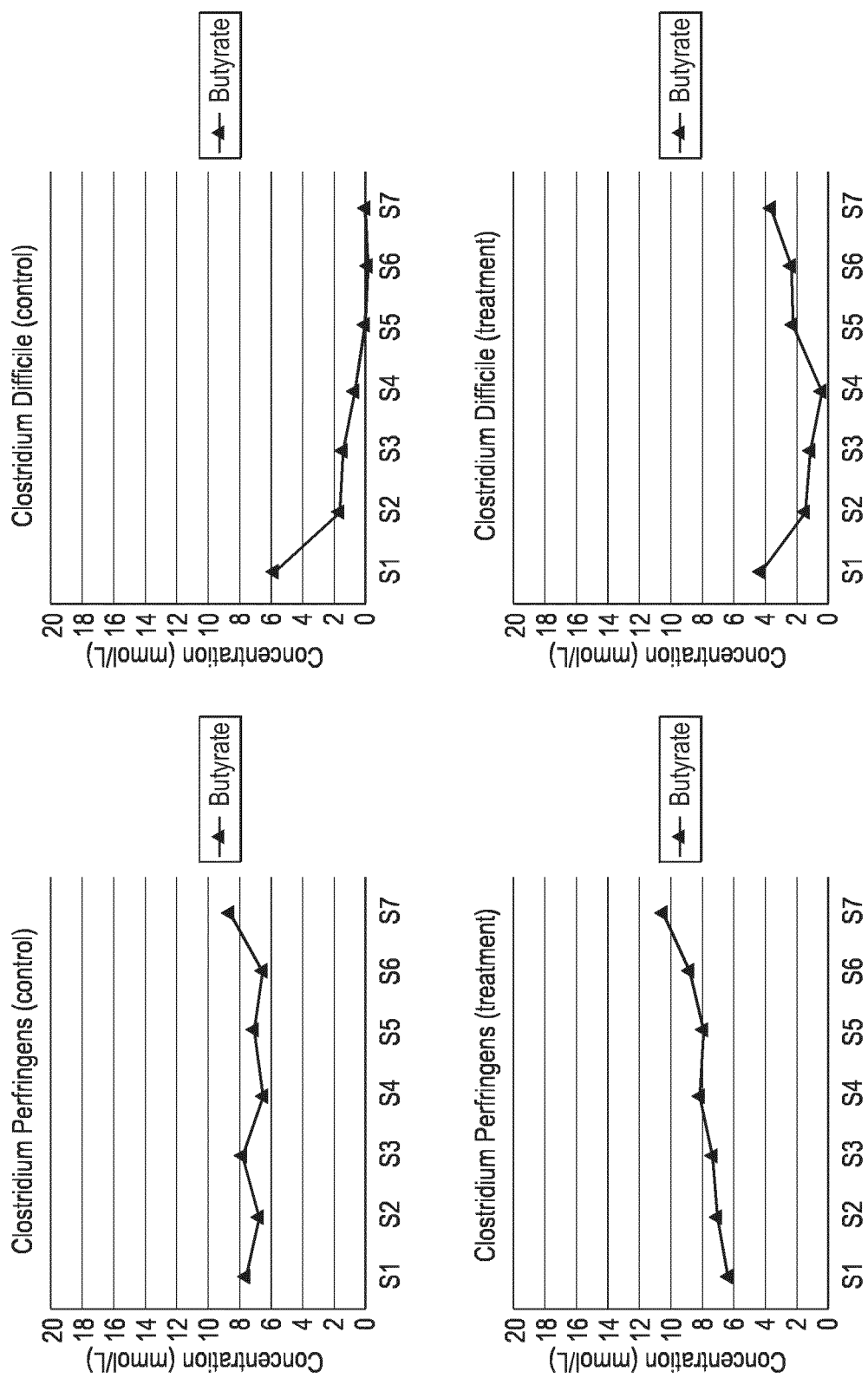
FIG. 4 shows graphs of butyrate concentrations for each daily sample S1-S7 for a control SHIME and a SHIME in which the fiber blend was used for each of V1 and V2.

With respect to SCFAs, samples were collected daily to analyze the concentration of acetic acid, propionic acid, and butyric acid. In FIG. 3, the data is presented as total SCFA, acetate, propionate and butyrate production per day of the TWINSHIME experiment. FIG. 4 focuses exclusively on butyrate production. As mentioned above, prebiotic properties are evaluated by a relative increase of propionate and/or butyrate in the total SCFA production.

Under normal conditions (no antibiotic treatment in the SHIME vessel V1 with *C. perfringens*, left graphs of FIG. 3) the addition of the fiber blend led to a higher SCFA production. This SCFA production was disrupted by the antibiotic treatment as shown in the SHIME vessel V2 with *C. difficile* (right graphs of FIG. 3). When comparing the fiber blend treatment to the control starting from the sample S5, improved recovery of SCFA production from the fiber blend is evident.

Figure 5:
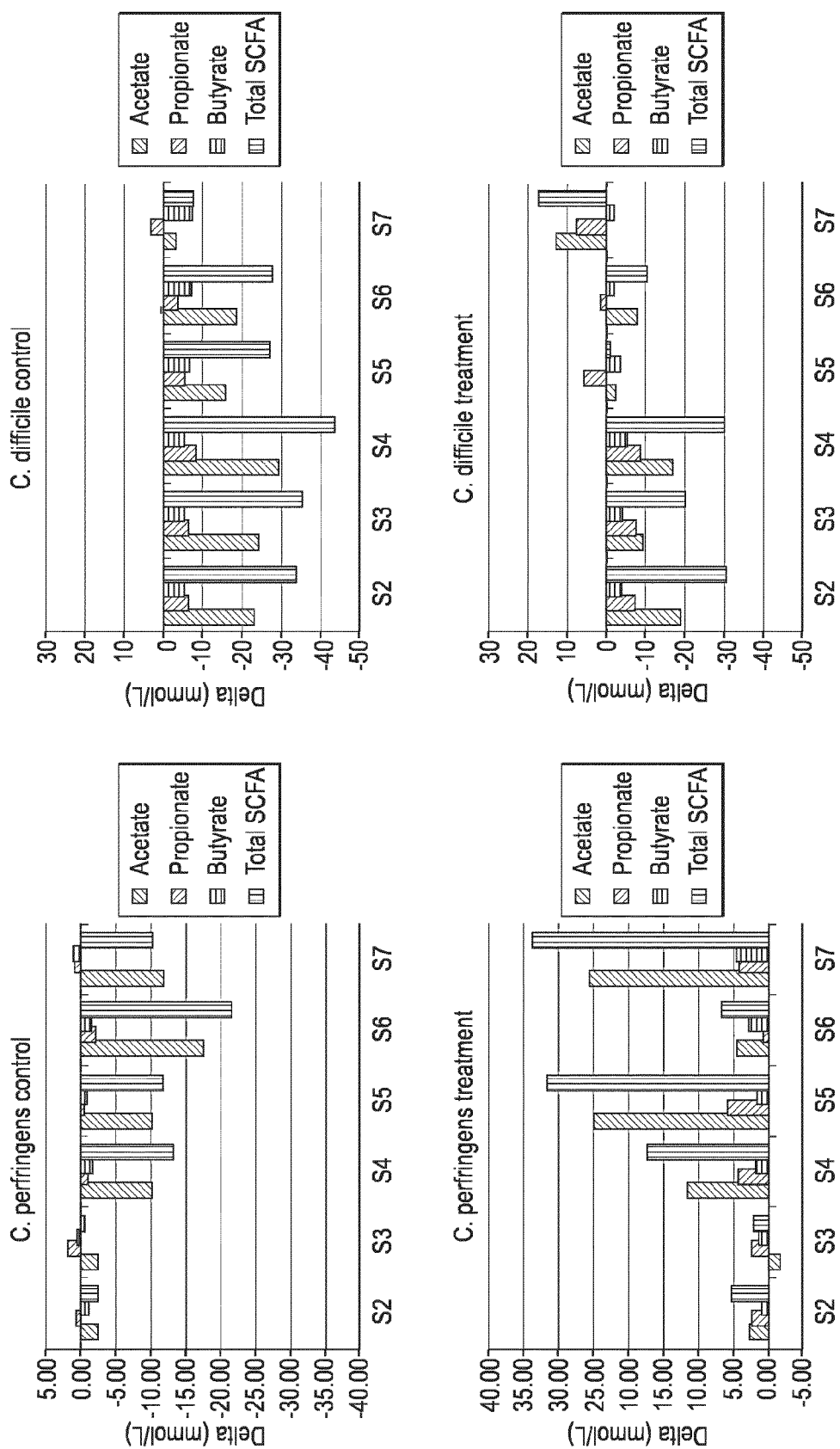
FIG. 5 shows bar charts of the change in SCFA production for each daily sample S2-S7 for a control SHIME and a SHIME in which the fiber blend was used for each of V1 and V2 using the values of sample S1 as baseline, with the addition of the fiber blend between S3 and S4.

The same positive effect of the fiber blend is shown in FIG. 5 where the data on SCFA production is presented as a delta using as baseline the values of the sample S1. For each daily sample S1-S7, the data from left to right is acetate, propionate, butyrate and total SCFA concentration.

Based on the data regarding SCFA production, the following conclusion can be reached: the fiber blend treatment improves the SCFA production under physiological conditions of the gastrointestinal tract and, when an antibiotic is dosed, helps to quickly restore and improve the normal functionality in a couple of days.

Results—Lactate

Figure 6:
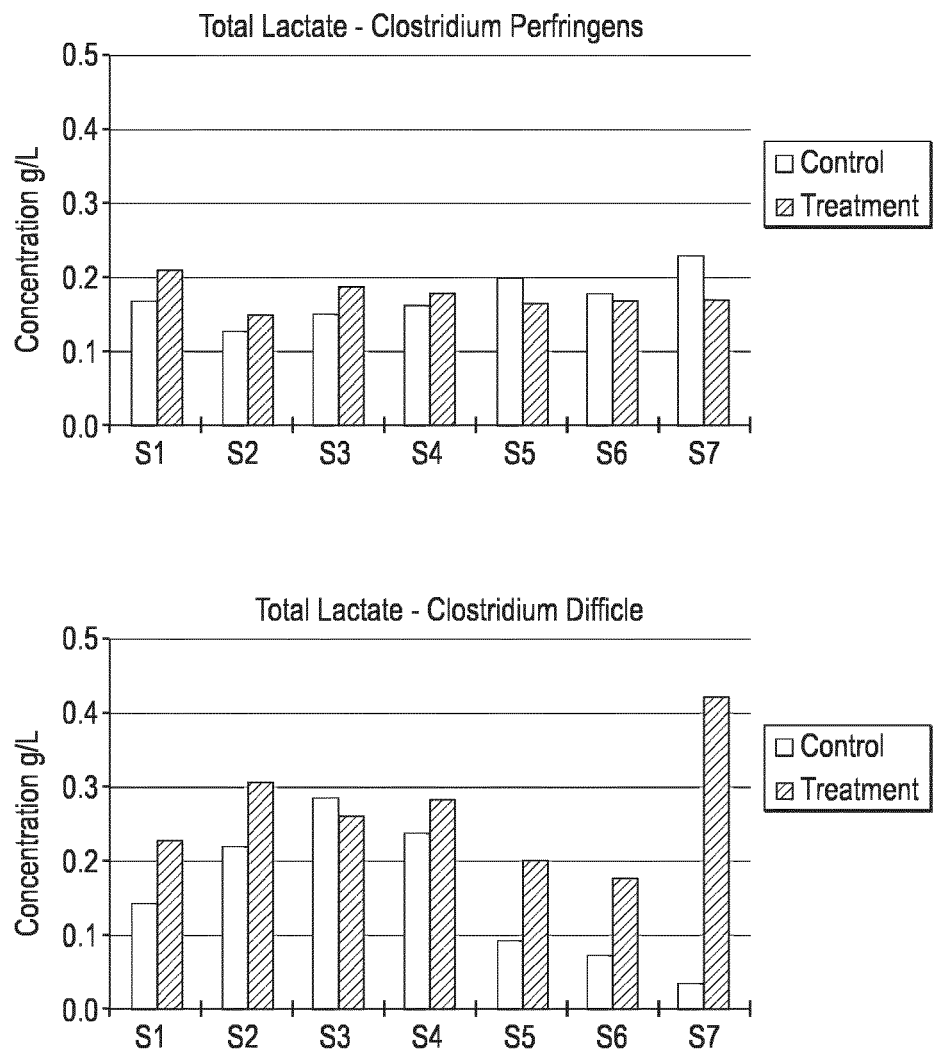
FIG. 6 shows bar charts of lactate concentrations for each daily sample S1-S7 for a control SHIME and a SHIME in which the fiber blend was used for each of V1 and V2.

The human intestine harbors both lactate-producing and lactate-utilizing bacteria. Lactate is produced by lactic acid bacteria and decreases the pH of the environment acting also as an antimicrobial agent. Lactate can also be rapidly converted to acetate, butyrate, and propionate by other microorganisms. The analysis of lactate concentrations in the experiment is presented in FIG. 6. For each daily sample S1-S7, the left bar is the control sample and the right bar is the fiber blend treatment sample.

In absence of an antibiotic treatment (*C. perfringens* SHIME V1, left graph of FIG. 6), the fiber blend slightly decreased the lactate production ($p<0.05$ when considering the last 3 sampling points). In the SHIME vessel V2 with *C. difficile* (right graph of FIG. 6), the addition of the antibiotic led to an increase in lactate as evidenced by comparison of S1 with S2. This effect may be related to a disruption of the networking originally present among bacteria. Under these conditions, the addition of the fiber blend led to an increase in the lactate production as compared to the control situation ($p>0.05$, when considering the last 3 sampling points). This effect was very strong in the *C. difficile* SHIME V2.

Results—pH Variation

To ensure that optimal environmental conditions are maintained, the pH in a SHIME system is controlled by pH controllers in the range of 5.6-5.8 for the ascending colon. However, upon stabilization of the microbial community in the different reactors two weeks after inoculation, the microbial community can auto-regulate itself, and acid-base consumption is normally low. Nevertheless, during a treatment, when bacteria adapt and produce, for example, increased amounts of SCFA, the environment in the reactors may acidify, which results in additional pH control by more administration of base to the respective reactors. In this context, the degree of acidification during the experiment can be used as a measure of the intensity of bacterial metabolism of the fiber blend. Therefore, the consumption of acid and base to maintain the pH in the correct range was measured for each daily sample S3-S7 and the data is reported in FIG. 7.

Figure 7:
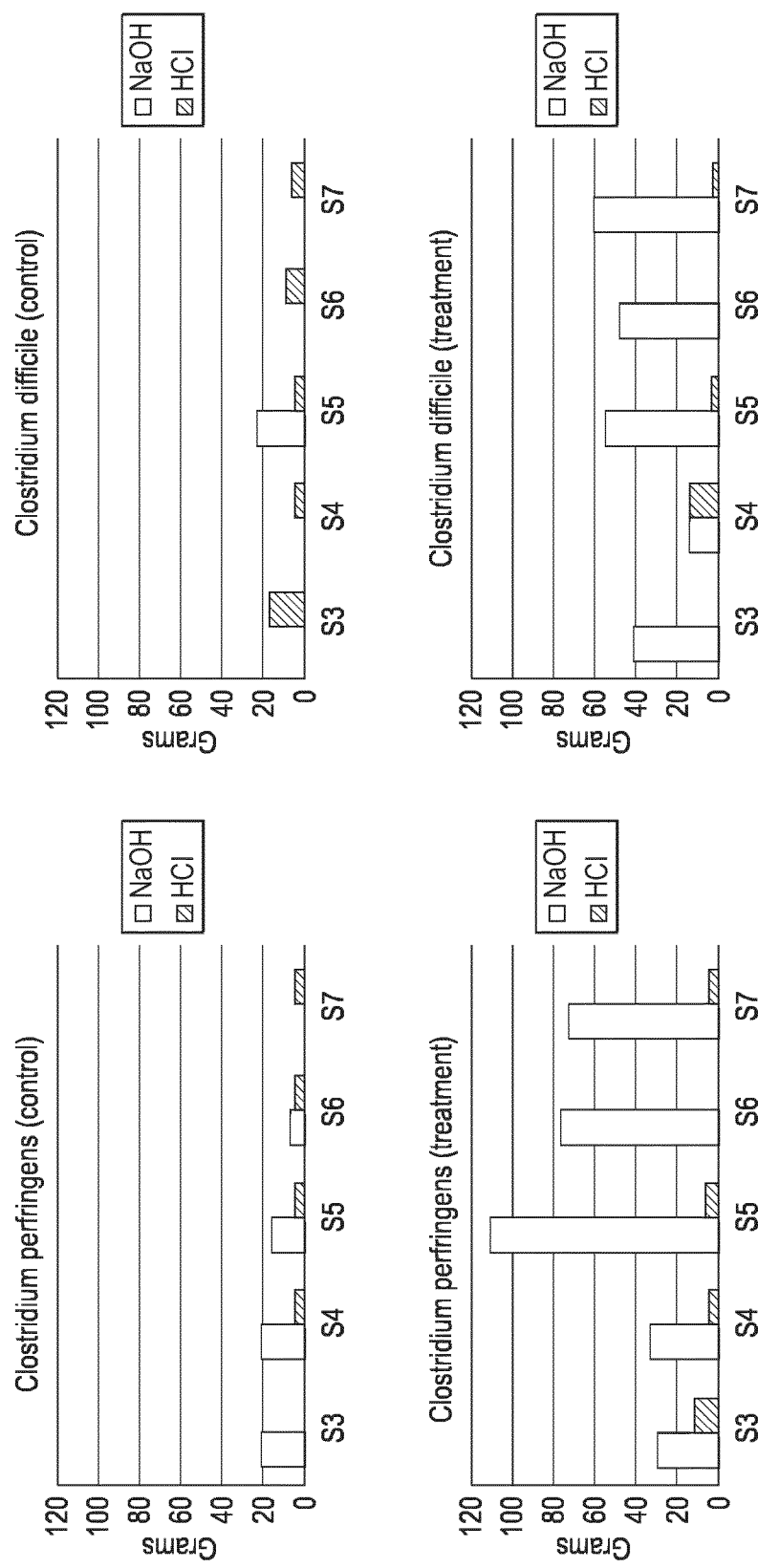
FIG. 7 shows acid-base consumption for each daily sample S3-S7 for a control SHIME and a SHIME in which the fiber blend was used for each of V1 and V2.
Figure 8A:
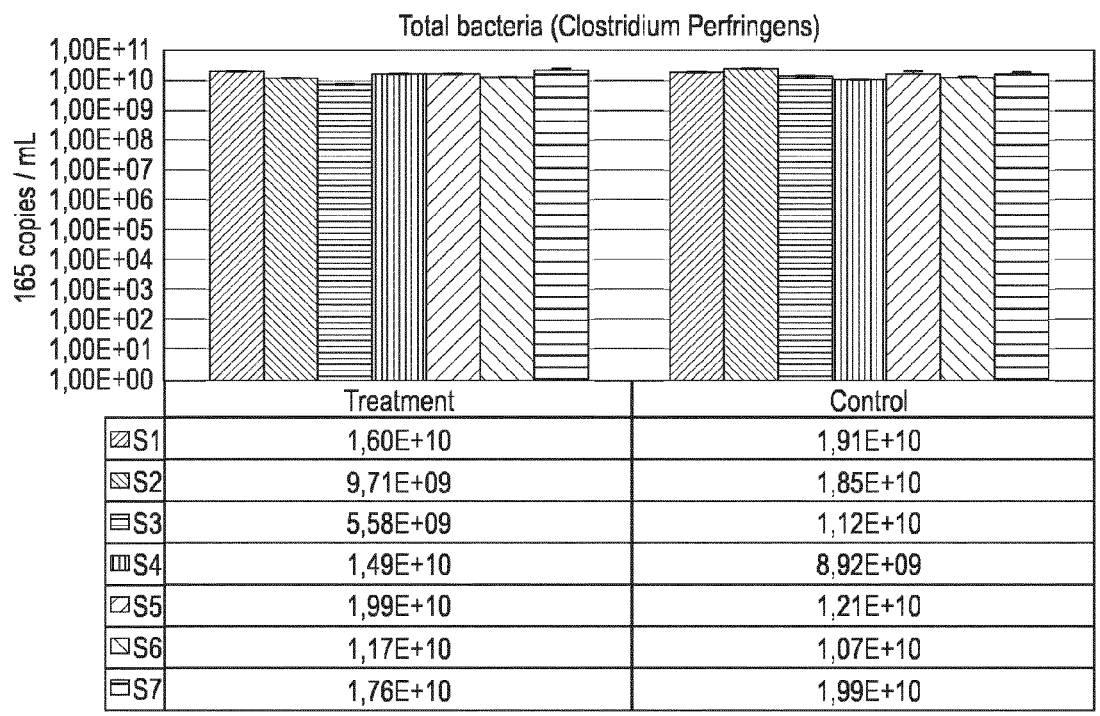
FIG. 8A shows qPCR data for the total bacteria for each daily sample S1-S7 for a control SHIME and a SHIME in which the fiber blend was used for each of V1 and V2.
Figure 8A:
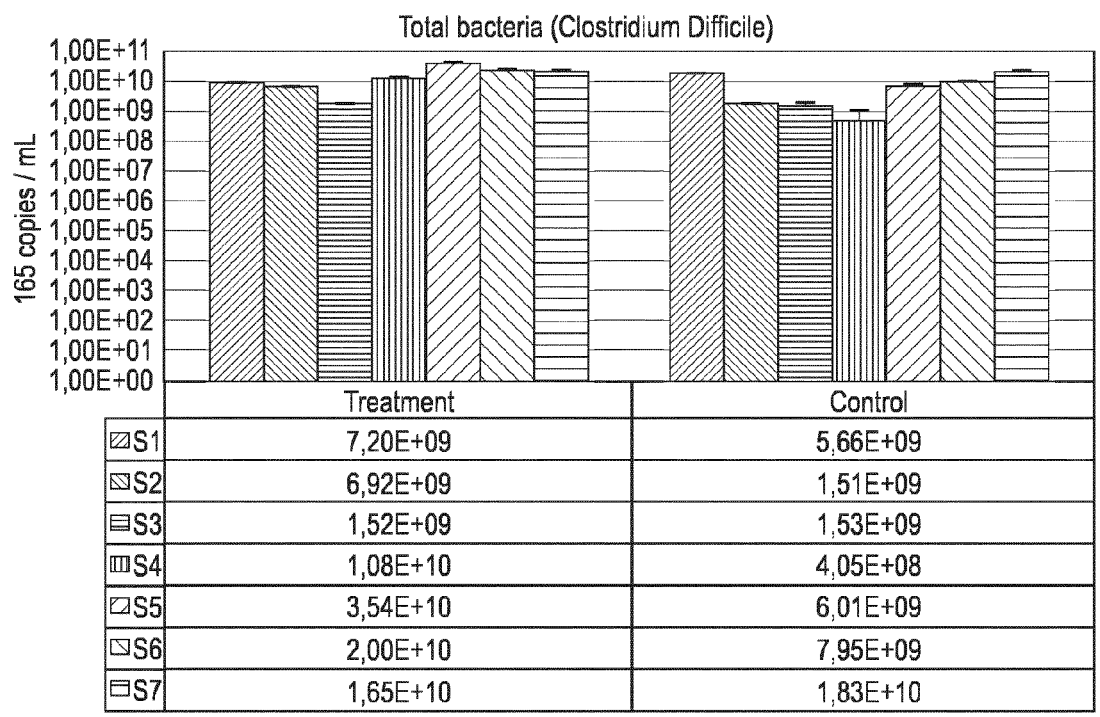
Figure 8B:
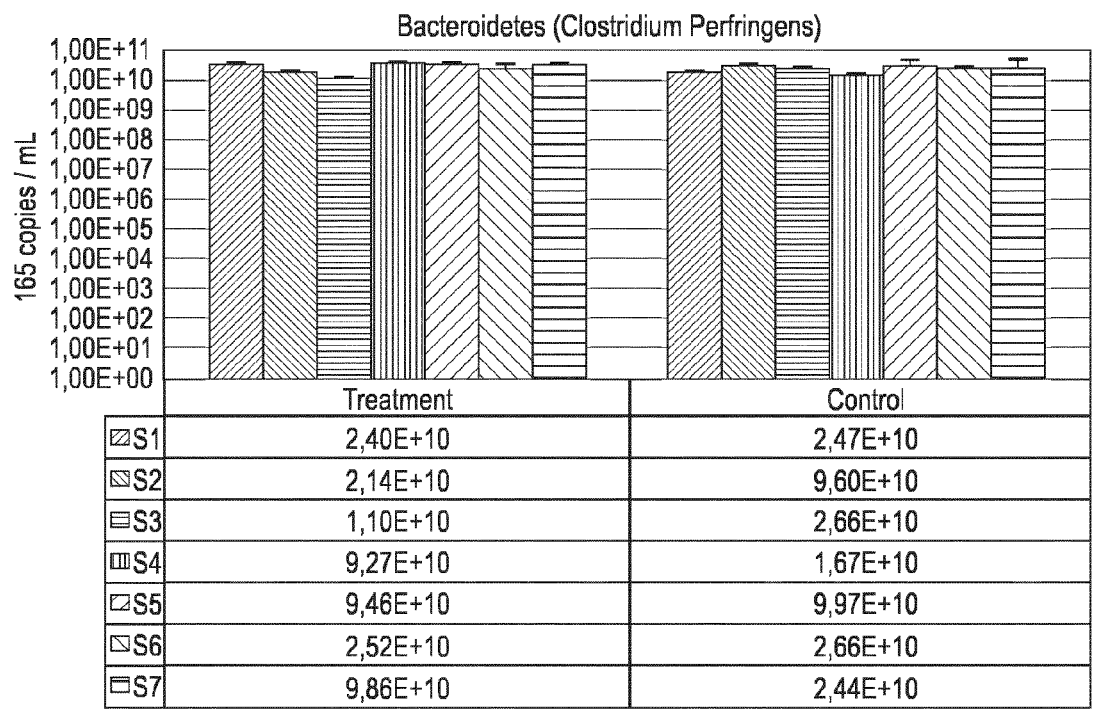
FIG. 8B shows qPCR data for the total Bacteriodetes for each daily sample S1-S7 for a control SHIME and a SHIME in which the fiber blend was used for each of V1 and V2.
Figure 8B:
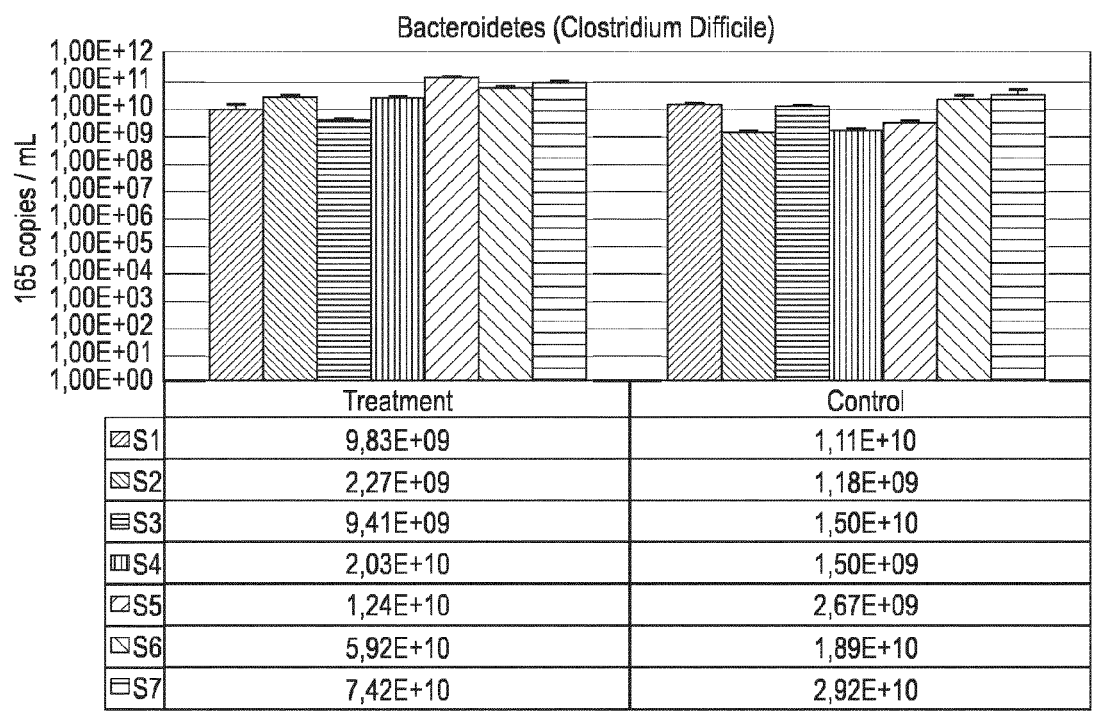
Figure 8C:
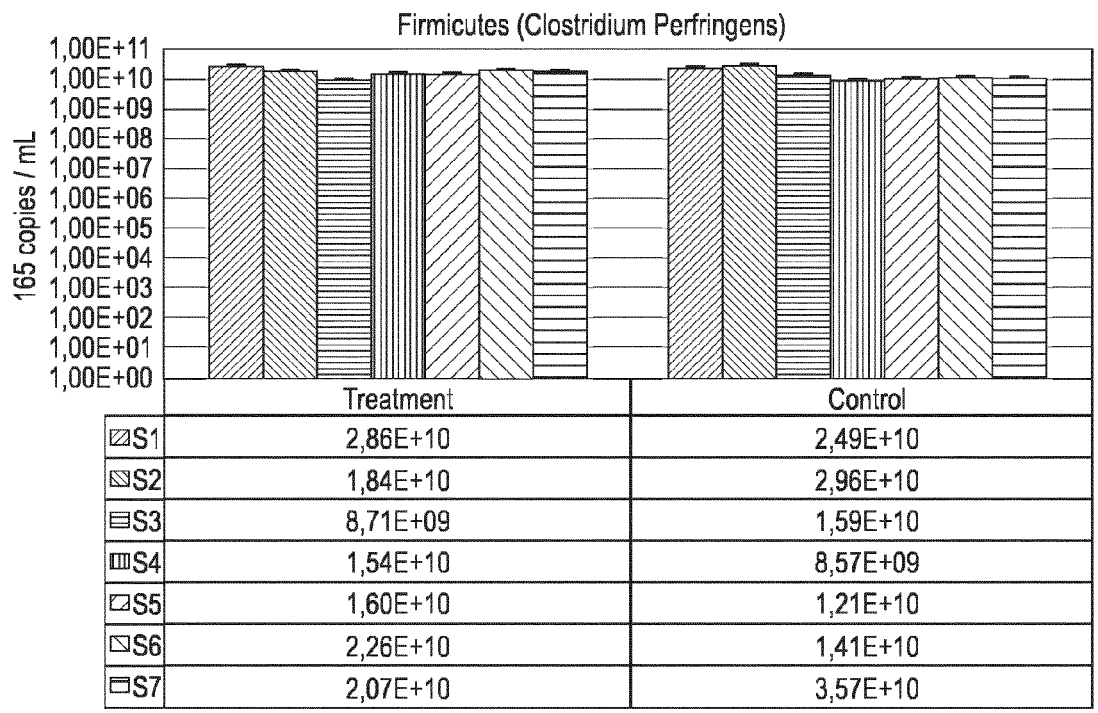
FIG. 8C shows qPCR data for the total Firmicutes for each daily sample S1-S7 for a control SHIME and a SHIME in which the fiber blend was used for each of V1 and V2.
Figure 8C:
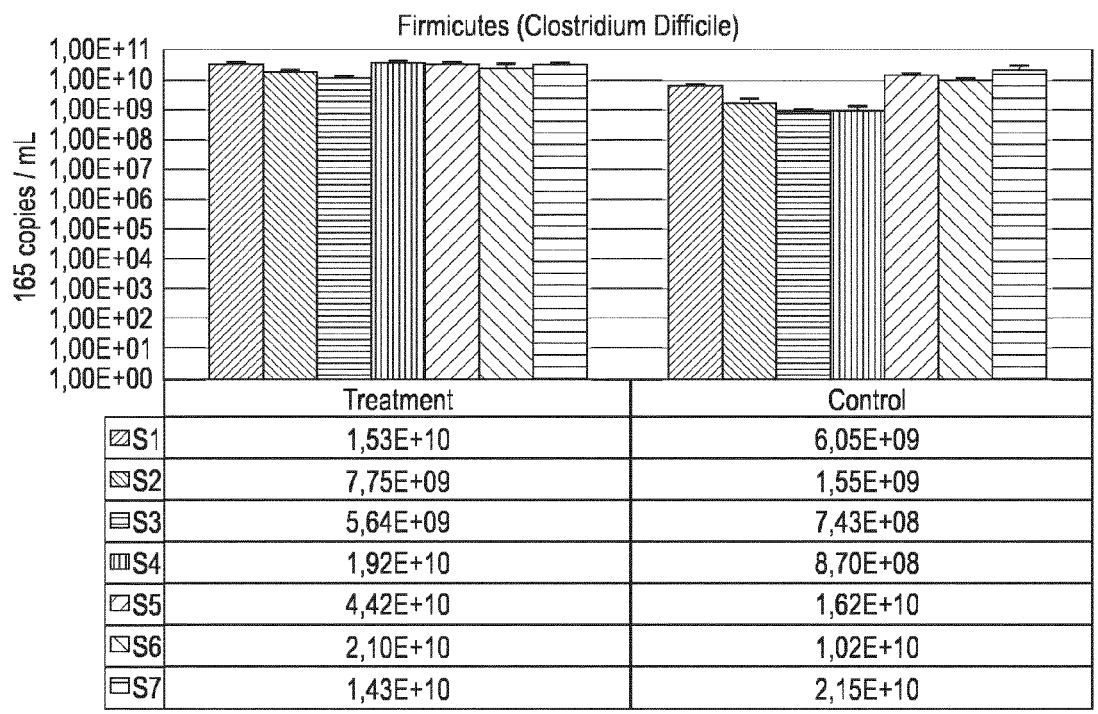
Figure 8D:
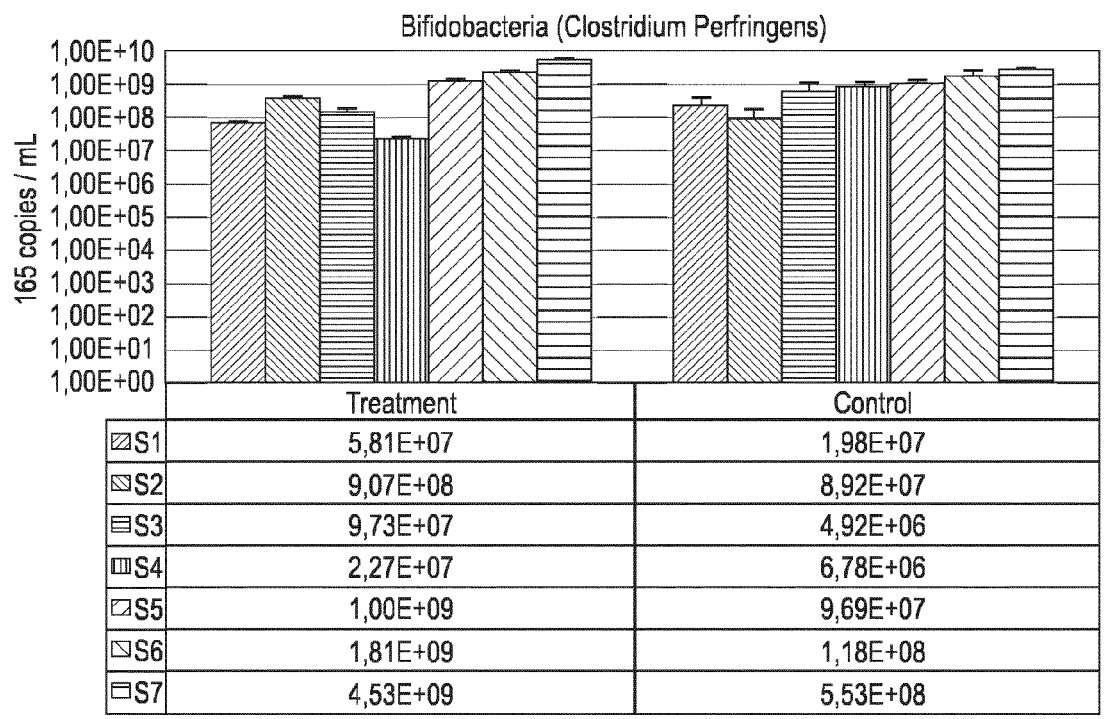
FIG. 8D shows qPCR data for the total *Bifidobacteria* for each daily sample S1-S7 for a control SHIME and a SHIME in which the fiber blend was used for each of V1 and V2.
Figure 8D:
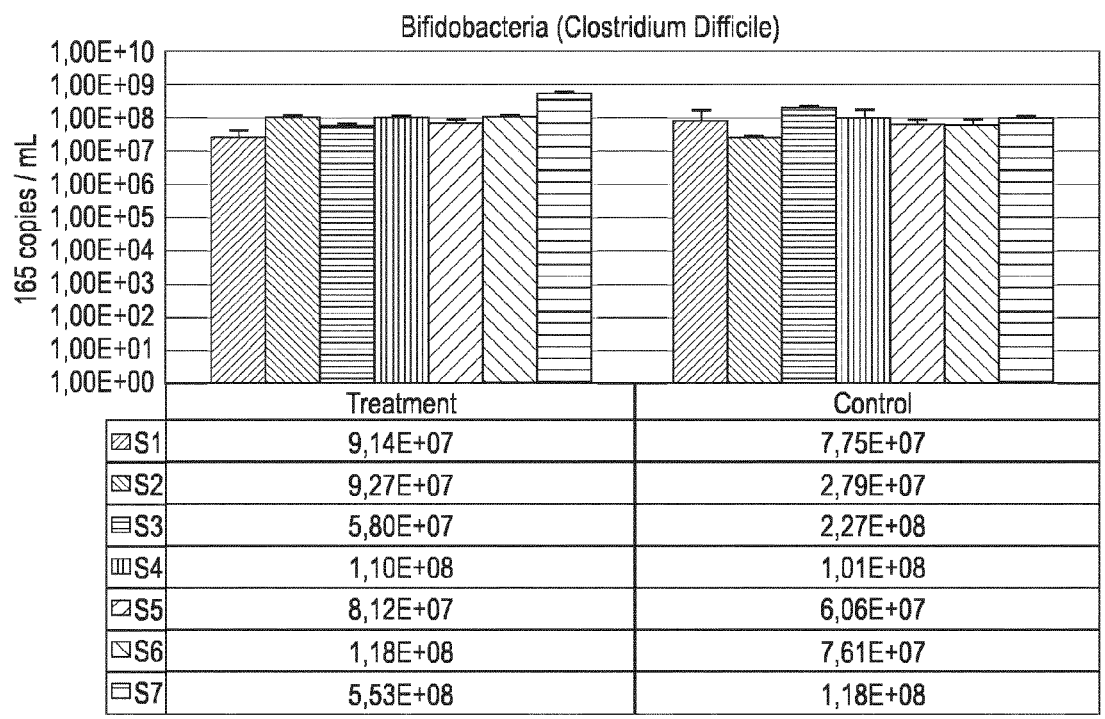
Figure 8E:
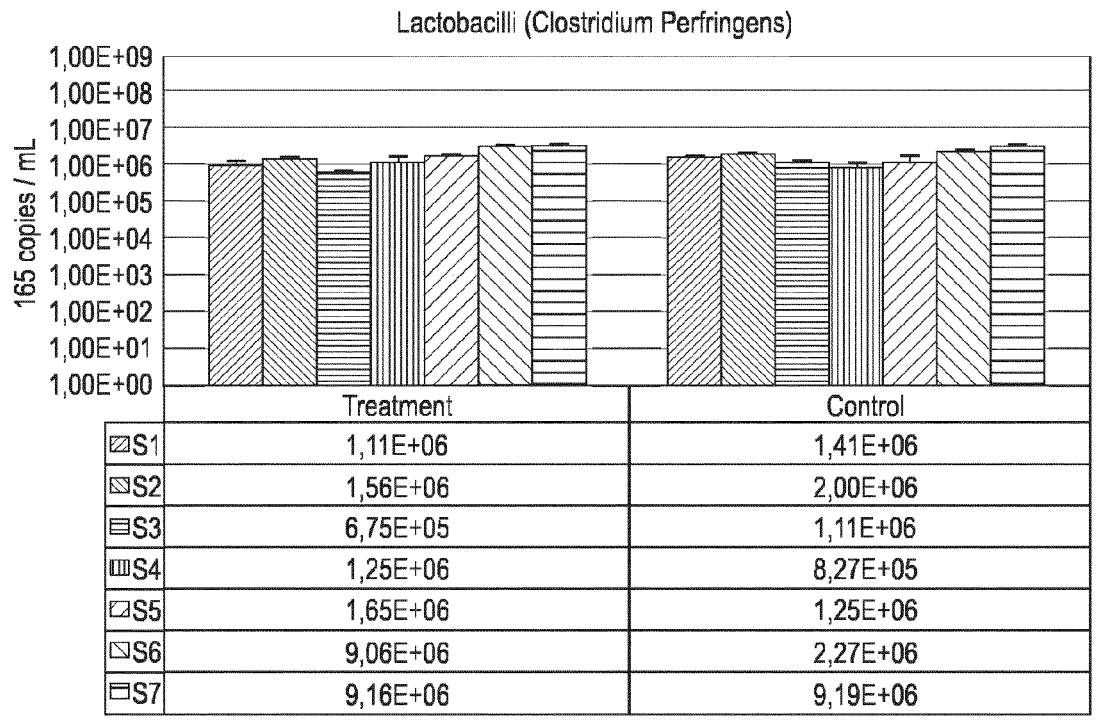
FIG. 8E shows qPCR data for the total *Lactobacilli* for each daily sample S1-S7 for a control SHIME and a SHIME in which the fiber blend was used for each of V1 and V2.
Figure 8E:
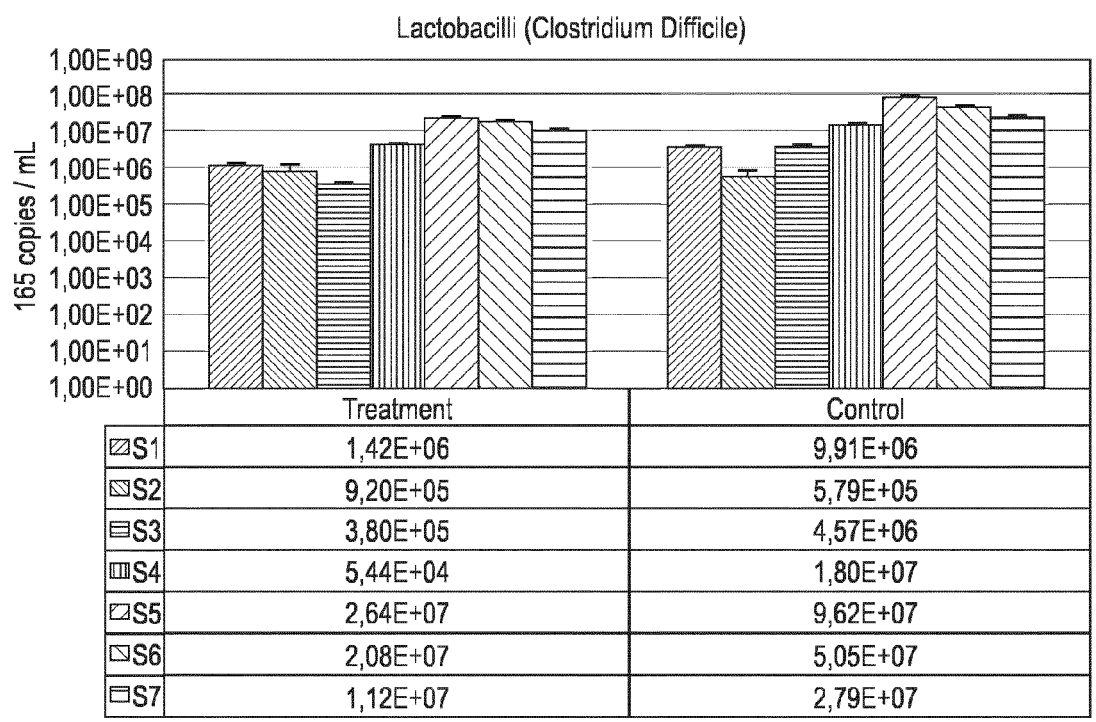

As shown in FIG. 7, in the *C. pefringens* SHIME vessel V1 (left graph of FIG. 7), the fiber blend treatment led to an improved acidification in the absence of an antibiotic treatment, as compared to the control ($p<0.05$). Following the antibiotic treatment in the *C. difficile* SHIME vessel V2 (right graph of FIG. 7), the addition of the fiber blend led to a quicker recovery of acidification as compared to the control ($p<0.05$). This data is in agreement with the improved production of SCFA and lactate discussed above.

Results—Microbial Community Composition

Samples were collected daily from the TWINSHIME to evaluate the effect of the fiber blend treatment on the luminal microbial community composition by means of quantitative polymerase chain reaction ("qPCR"). Specifically, qPCR was used to monitor total bacteria, *Bifidobacteria, Lactobacilli*, firmicutes, and bacteroidetes. qPCR is a molecular technique which is based on the amplification of specific bacterial sequences (165 rRNA genes), combined with the quantification of the number of these specific sequences in the microbial ecosystem at different time points. This technique is not dependent on the (lack of) culturability of the bacteria, so data generated with this method offers a more reliable overview on quantitative effects on the microbial community due to the fiber blend treatment.

Firmicutes and Bacteroidetes are the two most dominant bacterial phyla in the gut. Bacteroidetes are considered as very important saccharolytic fermenting bacteria, as a large part of the proteins codified by Bacteroidetes goes to breaking down polysaccharides and metabolizing their sugars. Some species belonging to this group are also associated with propionate production.

Firmicutes are users of the metabolic intermediates produced by the metabolism of Bacteroidetes. They include *Lactobacilli* and *Clostridia*. The latter are often considered to be negative for health because specific *Clostridia* are well-known pathogens. Yet, among the *Clostridia* are also several of the most important butyrate producers, a bacterial metabolite which is considered a key health beneficial compound.

Figure 9A:
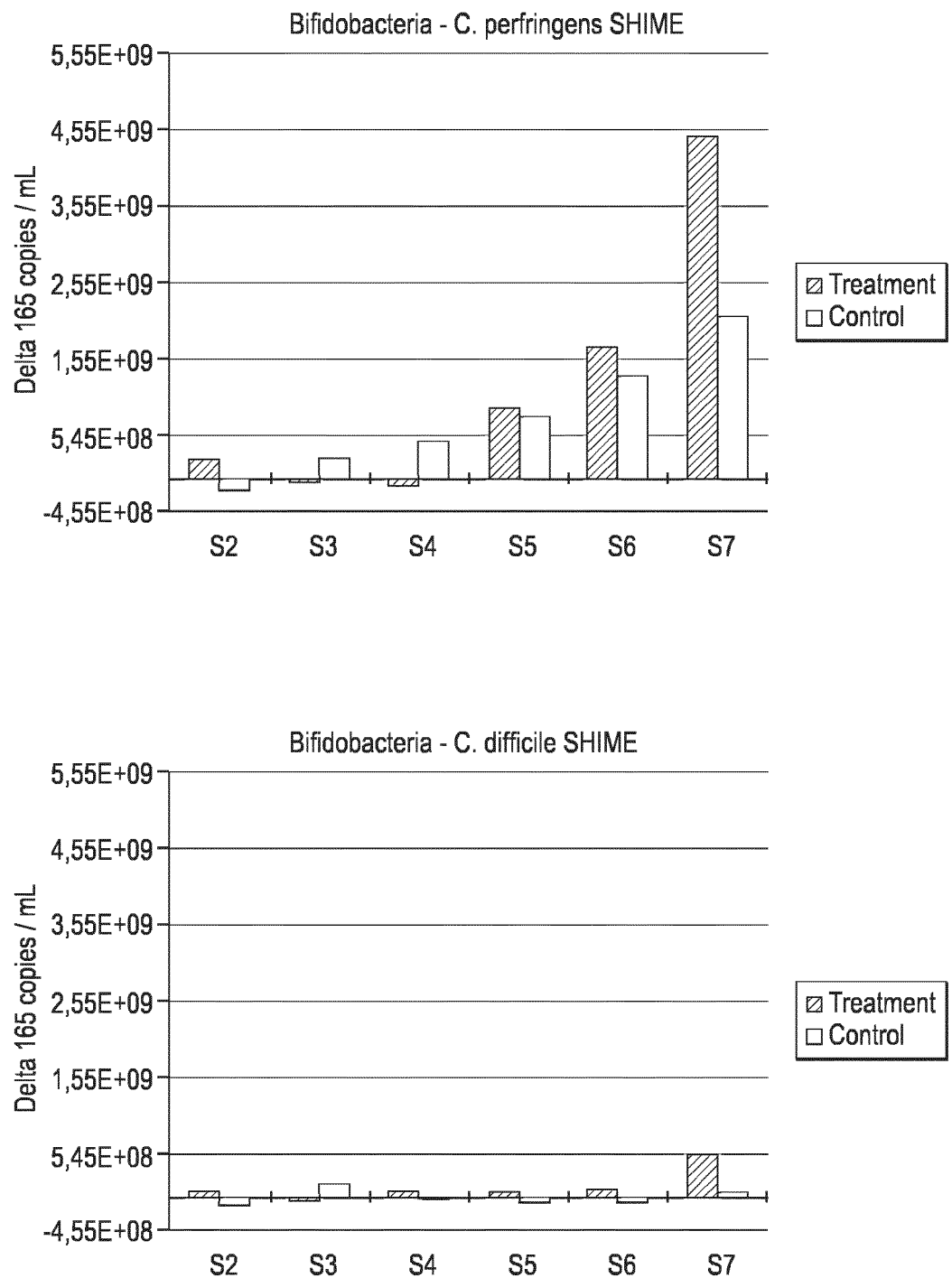
FIG. 9A shows change in concentration of *Bifidobacteria* for each daily sample S2-S7 for a control SHIME and a SHIME in which the fiber blend was used for each of V1 and V2 using the values of sample S1 as baseline.
Figure 9B:
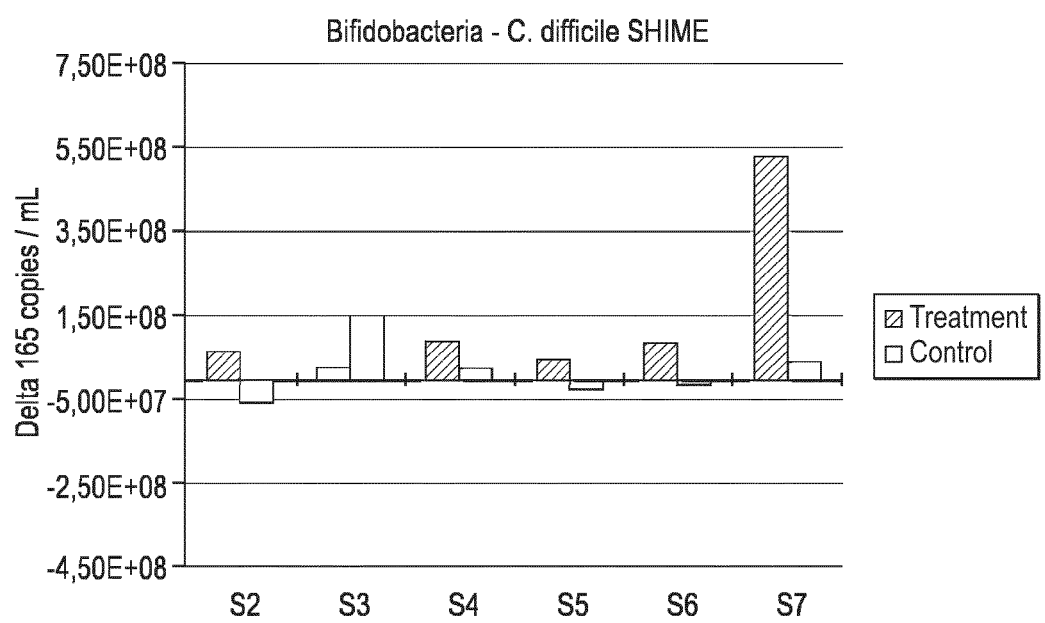
FIG. 9B shows change in concentration of *Bifidobacteria* for each daily sample S2-S7 for a control SHIME and a SHIME in which the fiber blend was used for V2 using the values of sample S1 as baseline and using a different scale than FIG. 9A.
Figure 9C:
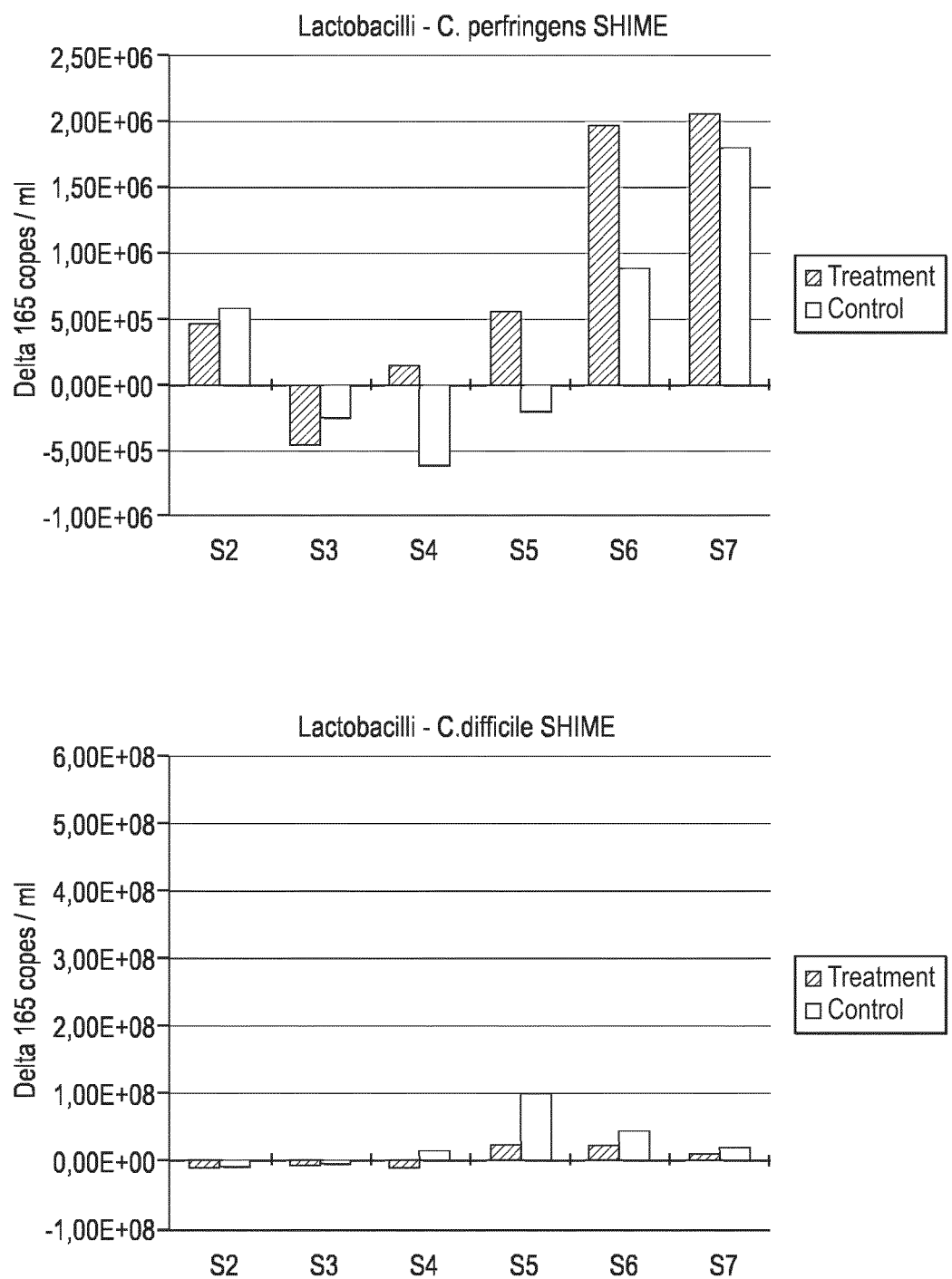
FIG. 9C shows change in concentration of *Lactobacilli* for each daily sample S2-S7 for a control SHIME and a SHIME in which the fiber blend was used for each of V1 and V2 using the values of sample S1 as baseline.
Figure 10:
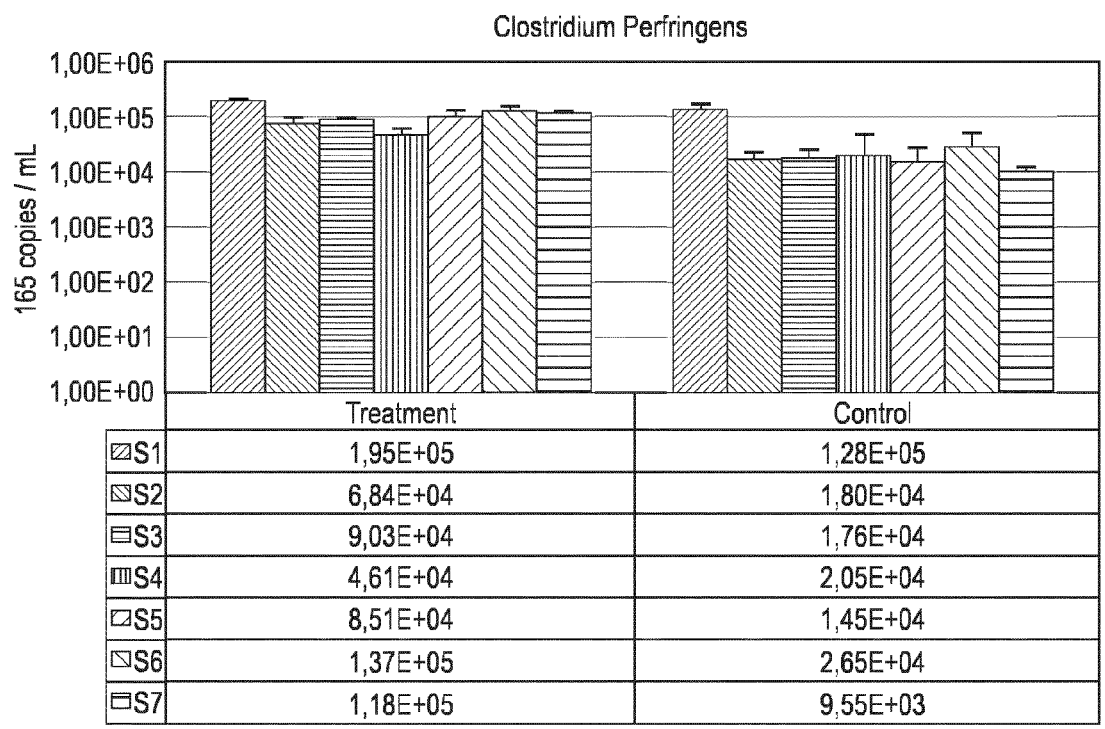
FIG. 10 shows qPCR data for *C. pefringens*, *C. difficile* and *K. pneumoniae* for each daily sample S1-S7 for a control SHIME and a SHIME in which the fiber blend was used for V1 and V2.
Figure 10:
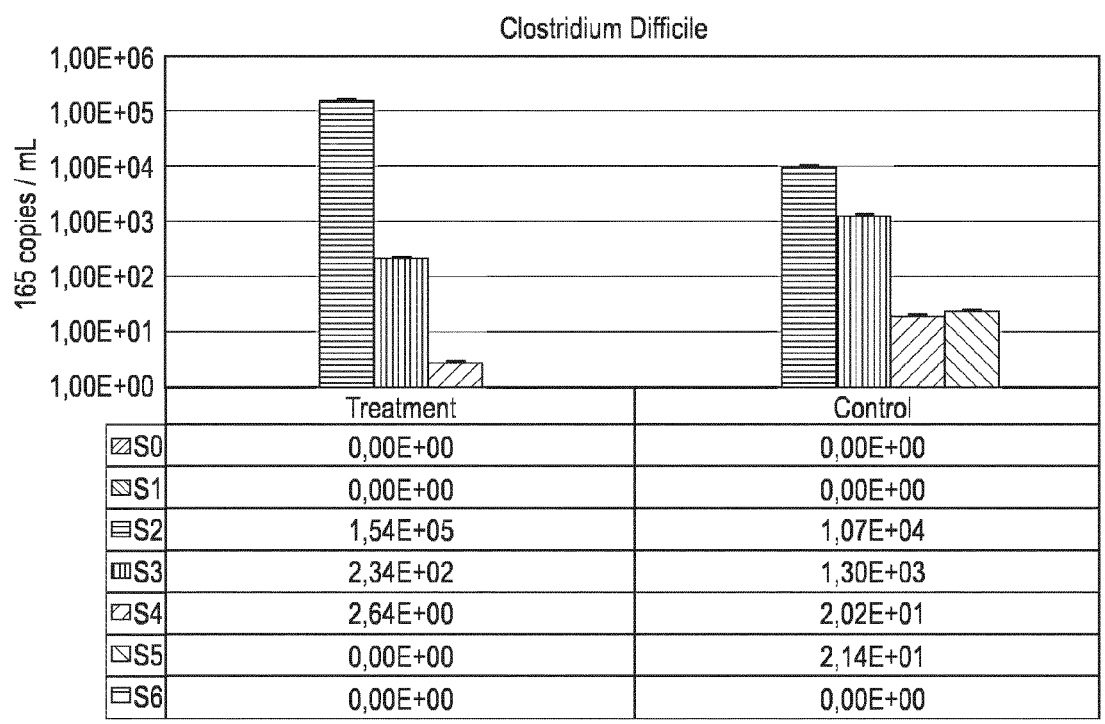

The effect of the antibiotic treatment and the recovery of the microbial community following the fiber blend treatment were followed using qPCR protocols specific for total bacteria, Bacteroidetes, Firmicutes, *Bifidobacteria* and *Lactobacilli*. FIGS. 8A-8E report the concentrations of these microbial groups for each daily sample S1-S7 (S1 at far left, progressing to S7 at far right), and FIGS. 9A-9C present the data for *Bifidobacteria* and *Lactobacilli* using sample S1 as the baseline for each reactor. Moreover, the effect of the fiber blend on the 2 pathogens, as compared to the control, was also investigated with specific qPCR protocols, and the results are shown in FIG. 10.

Based on the data regarding the microbial community composition, the following conclusions related to the use of the fiber blend can be reached. The number of total bacteria had an improved recovery following an antibiotic treatment in the *C. difficile* SHIME vessel V2 in which the fiber blend was added, as compared to the control SHIME.

For Bacteroidetes concentration, there was a limited effect in the absence of an antibiotic treatment. The number of Bacteroidetes (carbohydrate degraders) had an improved recovery following an antibiotic treatment in the *C. difficile* SHIME vessel V2 in which the fiber blend was added, as compared to the control SHIME.

For Firmicutes concentration, no effect was seen in the absence of an antibiotic treatment. The number of Firmicutes had an improved recovery following an antibiotic treatment in the *C. difficile* SHIME vessel V2 in which the fiber blend was added, as compared to the control SHIME.

For *Bifidobacteria* concentration, the *C. perfringens* SHIME vessel V1 without antibiotic treatment had a possible qualitative change and then a delayed bifidogenic effect from the fiber blend. As a result of the fiber blend, *Bifidobacteria* were resistant to the antibiotic mix. In the *C. difficile* SHIME vessel V2, a bifidogenic effect from the fiber blend was observed at the end of the week. For *Lactobacilli* concentration, the *C. perfringens* SHIME V1 without antibiotic treatment did not have a clear lactobacillogenic effect from the fiber blend. In samples S5 and S6, the concentration of *Lactobacilli* is slightly higher in the fiber blend treatment compared to the control but then, at sampling point S7, the values are identical. In the presence of an antibiotic treatment, a fast recovery of *Lactobacilli* was observed both in the control and the fiber blend treatment.

The washout of *C. difficile* from the system was faster during the treatment with the fiber blend. This result is made stronger by the fact that the concentration of *C. perfringens* in the SHIME that underwent the treatment with the fiber blend was 1 Log higher than the control at S3.

Figure 11:
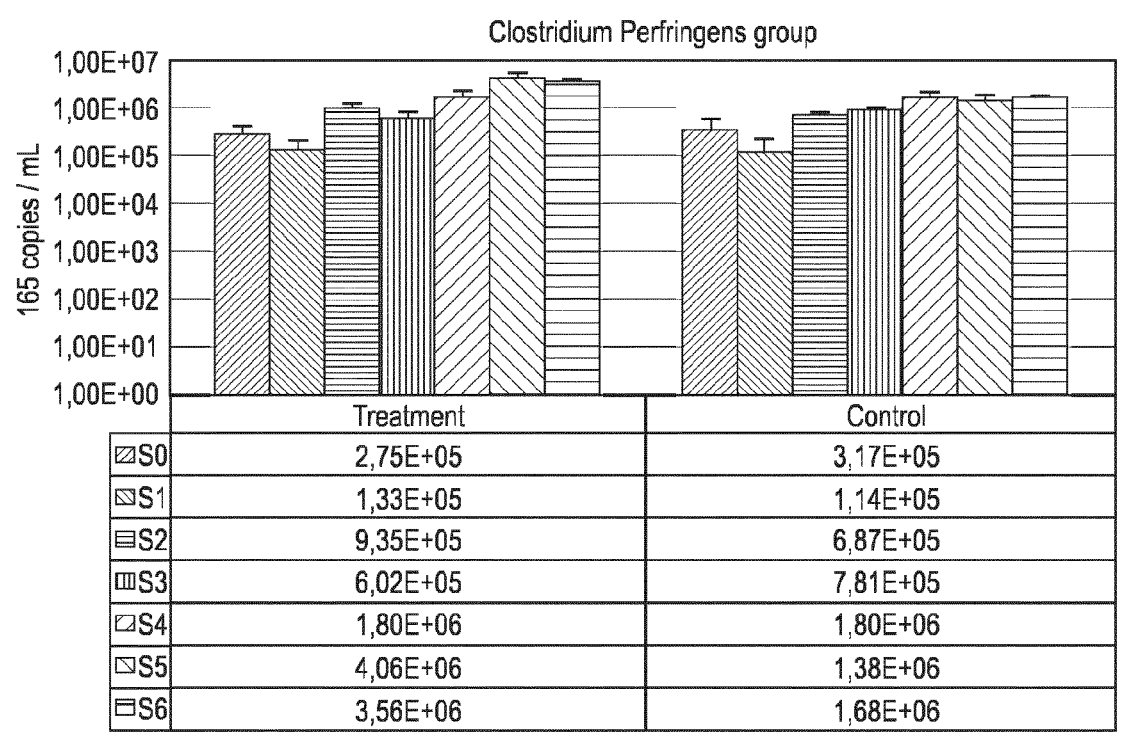
FIG. 11 shows qPCR data for the *C. pefringens* group for each daily sample S0-S6 for a control SHIME and a SHIME in which the fiber blend was used for V1.

Finally, the genus *Clostridium* is divided in clusters, and *C. perfringens* is the strain of a group that includes some bacteria with interesting properties, such as *C. butyricum* that is a butyrate-producing species commercially used as probiotic and *C. homopropionicum* that is a propionate-producing bacteria. Therefore, an extra qPCR was conducted with primers for the *C. perfringens* group. Results are shown in FIG. 11. The treatment with the fiber blend led to a higher concentration of bacteria belonging to the *C. perfringens* cluster, as compared to the control (p=0.015 when considering the last 2 sampling points).

Example 2

In Vitro Evaluation of Soluble Fibers Using the M-SHIME Experimental Design

The application of well-designed, continuous in vitro models of the gastrointestinal tract allows the in-depth study of the biological activity of selected molecules in the gut under representative environmental conditions. This study investigated the effects of soluble fibers on outcomes such as *C. difficile* concentrations, toxin levels, and recovery of the microbiota composition and functionality following antibiotic treatment.

The study examined an individual soluble fiber as well a blend of soluble fibers. The individual fiber is a FOS; the soluble fibers are FOS in an amount of about 41% by weight, acacia gum in an amount of about 41% by weight, and inulin in an amount of about 18% by weight (hereafter "Soluble Fiber Blend").

To study potential properties of the fibers in detail using an in vitro setup, a continuous model was used. Most in vitro strategies are limited to modeling of the luminal microbial community and do not allow culturing of the fraction of microorganisms which adhere to the gut mucosa. This means that an important part of the gut ecosystem is not taken into account. Therefore, this study employed an adaptation of the SHIME (termed the M-SHIME) which allows culturing of both the luminal and mucus-associated microbial community.

Figure 12:
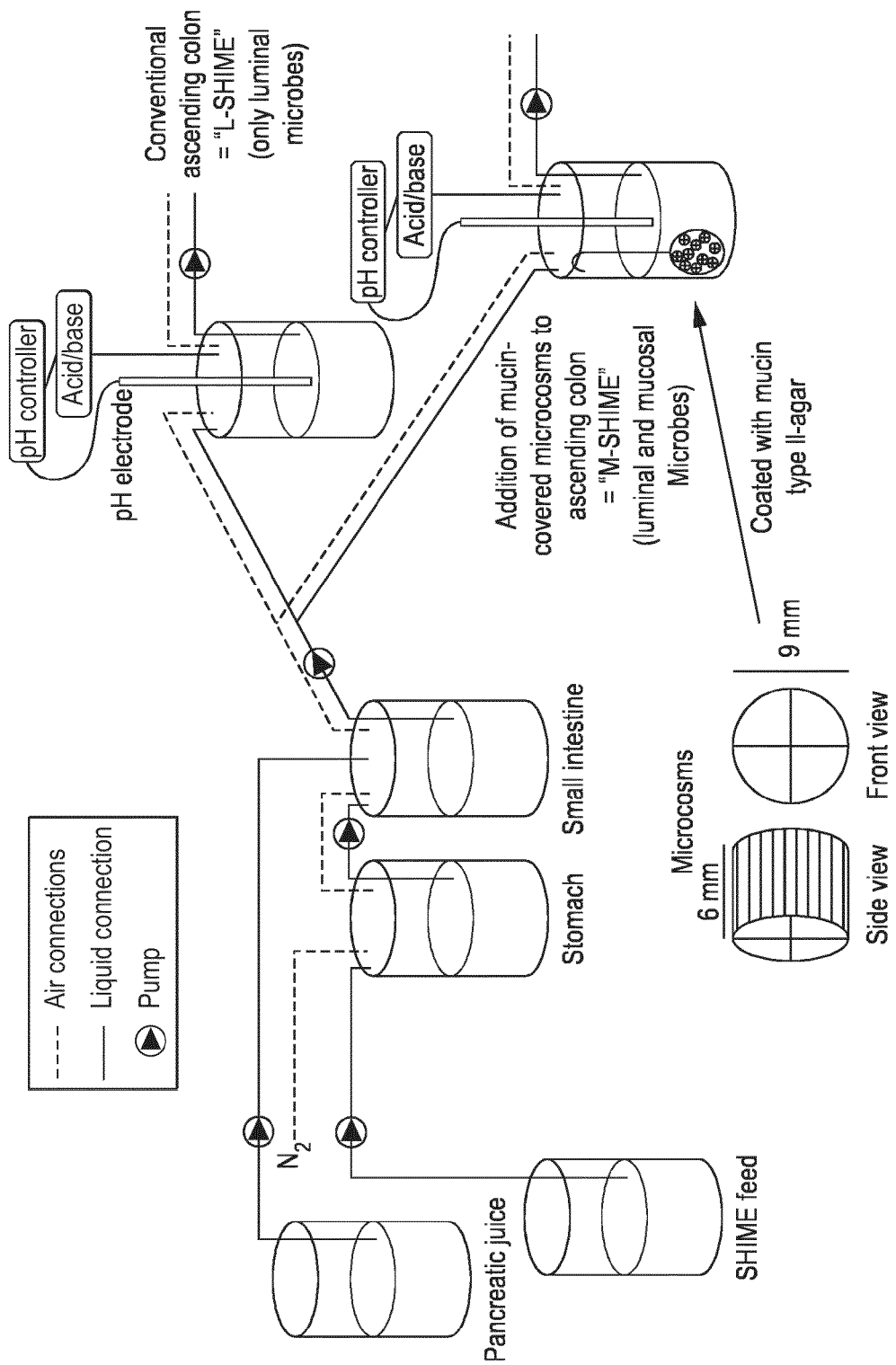
FIG. 12 shows an example set up of adapted Simulator of the Human Intestinal Microbial Ecosystem ("M-SHIME") which allows culturing of both the luminal and mucus-associated microbial community. Three SHIME systems are configured in parallel ("Triple-SHIME") to attain identical environmental conditions for all systems.

The M-SHIME was developed as an adaptation of the standard SHIME, with the additional simulation of a gut surface (i.e. plastic beads covered with a mucin agar layer; 50% of them are replaced every 48 hours thus providing a constant surface for bacteria adhesion) (FIG. 12). This provides a more ecologically-relevant gut microbial community, increasing the survival in the system of those species (e.g. *lactobacilli*) that otherwise would be quickly washed out. Inclusion of the mucosa compartment increases the value and modeling capacity of the SHIME® and allows evaluation of whether colonization of the probiotics/pathogens under study is limited to the gut lumen or whether the strains can efficiently adhere to the mucus layer and maintain themselves in the mucosa-associated microbial community. Moreover, allowing the bacteria to adhere may on the one hand increase their capacity to colonize the gut lumen, by better retention in the gut, and on the other hand it provides a more reliable simulation of the processes normally occurring in vivo.

Figure 13:
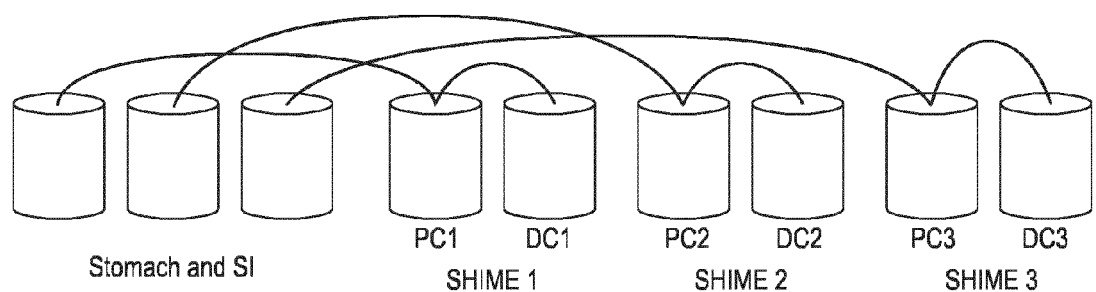
FIG. 13 shows a schematic representation of an M-SHIME which simulated 3 gastrointestinal tracts (Triple-SHIME) in terms of proximal and distal colon. Three SHIME systems were operated in parallel (SHIME 1=Soluble Fiber Blend; SHIME 2=FOS; SHIME 3=control [starch]).

The experiment utilized an M-SHIME which simulated 3 gastrointestinal tracts (Triple-SHIME) in terms of proximal and distal colon (in place of the classical ascending, transverse, and descending colon; FIG. 13. Three systems were operated in parallel (SHIME 1=Soluble Fiber Blend; SHIME 2=FOS; SHIME 3=control [starch]). Identical environmental conditions were obtained by identical pH and temperature control and by using pumps for liquid transfer between the reactors.

The first stage of the study was a start-up stage. After inoculation of the proximal colon reactors with an appropriate fecal sample (elder donor with a low concentration of *Bifidobacteria*), a two-week start-up period allowed the microbial community to differentiate in the different reactors depending on the local environmental conditions. Samples from the proximal and distal colon vessels were collected to perform the following analyses: 1) short chain fatty acid (SCFA); 2) pH variation; 3) toxins measurement (*C. difficile* toxins A and B) 4) qPCR for luminal bacteria (*lactobacilli, bifidobacteria*, total bacteria); 5) qPCR specific for *C. difficile* (luminal and mucosal); and 6) number of viable *C. difficile* CFU via selective plating.

Figure 14:
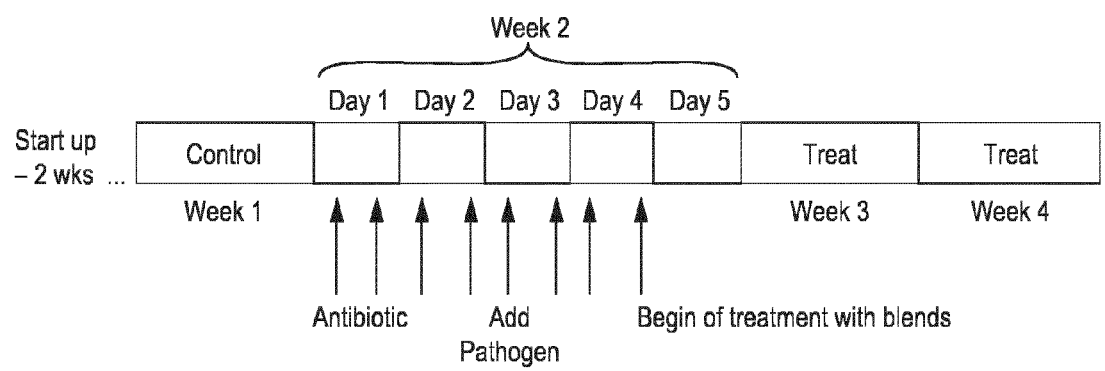
FIG. 14 shows a schematic representation of an example test protocol, as used in Example 2.

To evaluate the anti-pathogenic effect of the fibers, the pathogen *C. difficile* was added to vessels simulating the proximal and distal colons after an antibiotic treatment. The antibiotic treatment consisted of a mix of 40 ppm Amoxicillin, 40 ppm Ciprofloxacin, and 10 ppm Tetracycline, and was dosed twice on a single day to the 3 proximal and 3 distal colon vessels. The vessels were then inoculated with five doses of *C. difficile* over the course of 3 days, followed by addition of the fiber treatments or control for 2 weeks (FIG. 14).

The first objective of the study was to evaluate whether or not the fibers had an anti-pathogenic activity following antibiotic and *C. difficile* infection. The second objective was to evaluate the recovery of the microbiota composition (luminal and mucosal) and functionality after the antibiotic treatment and following the addition of the fiber blend.

Results—SCFA

Figure 15:
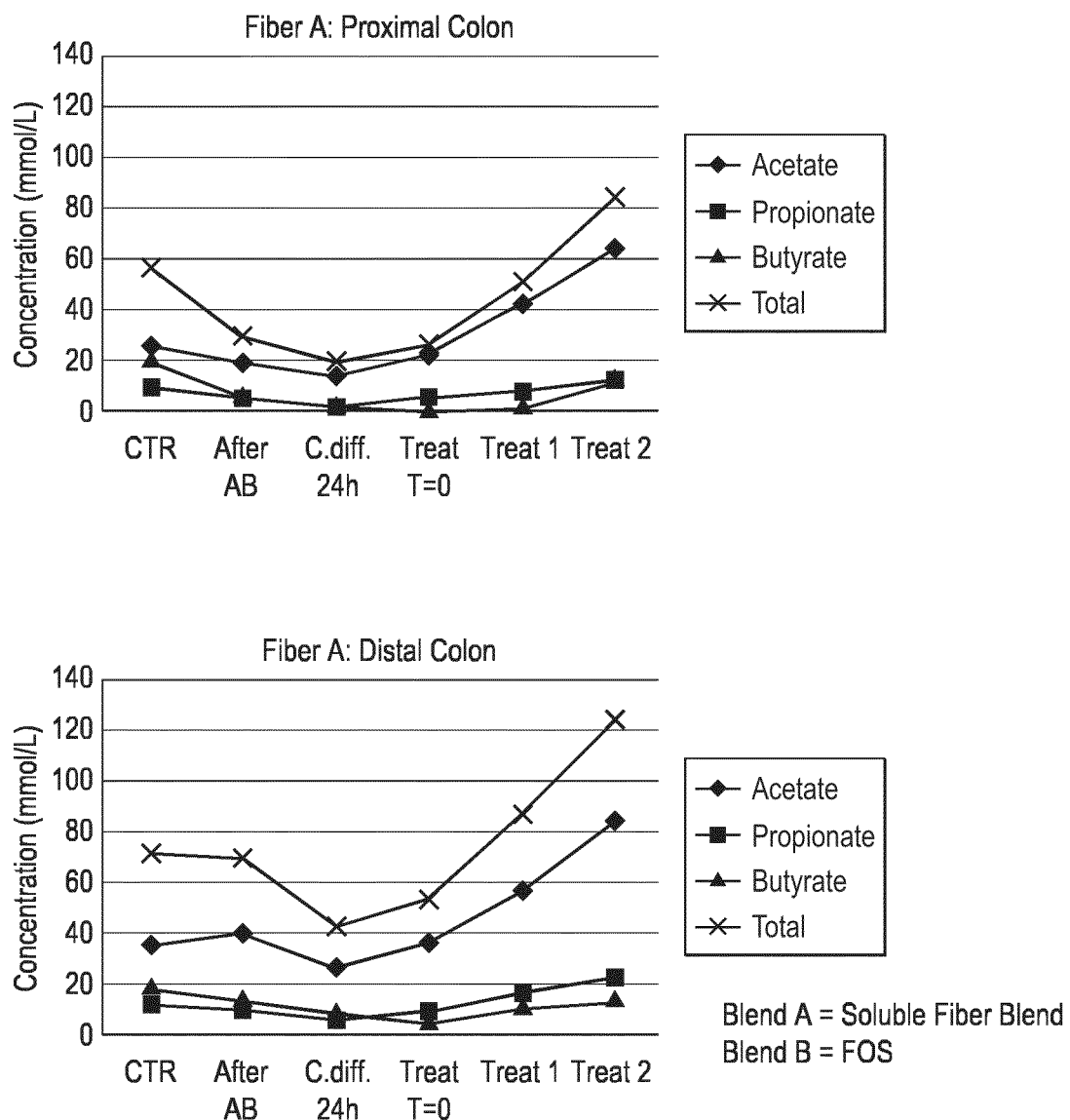
FIG. 15 shows graphs of concentrations of total SCFA, acetate, propionate and butyrate production per experiment week of the SHIME experiment.
Figure 15:
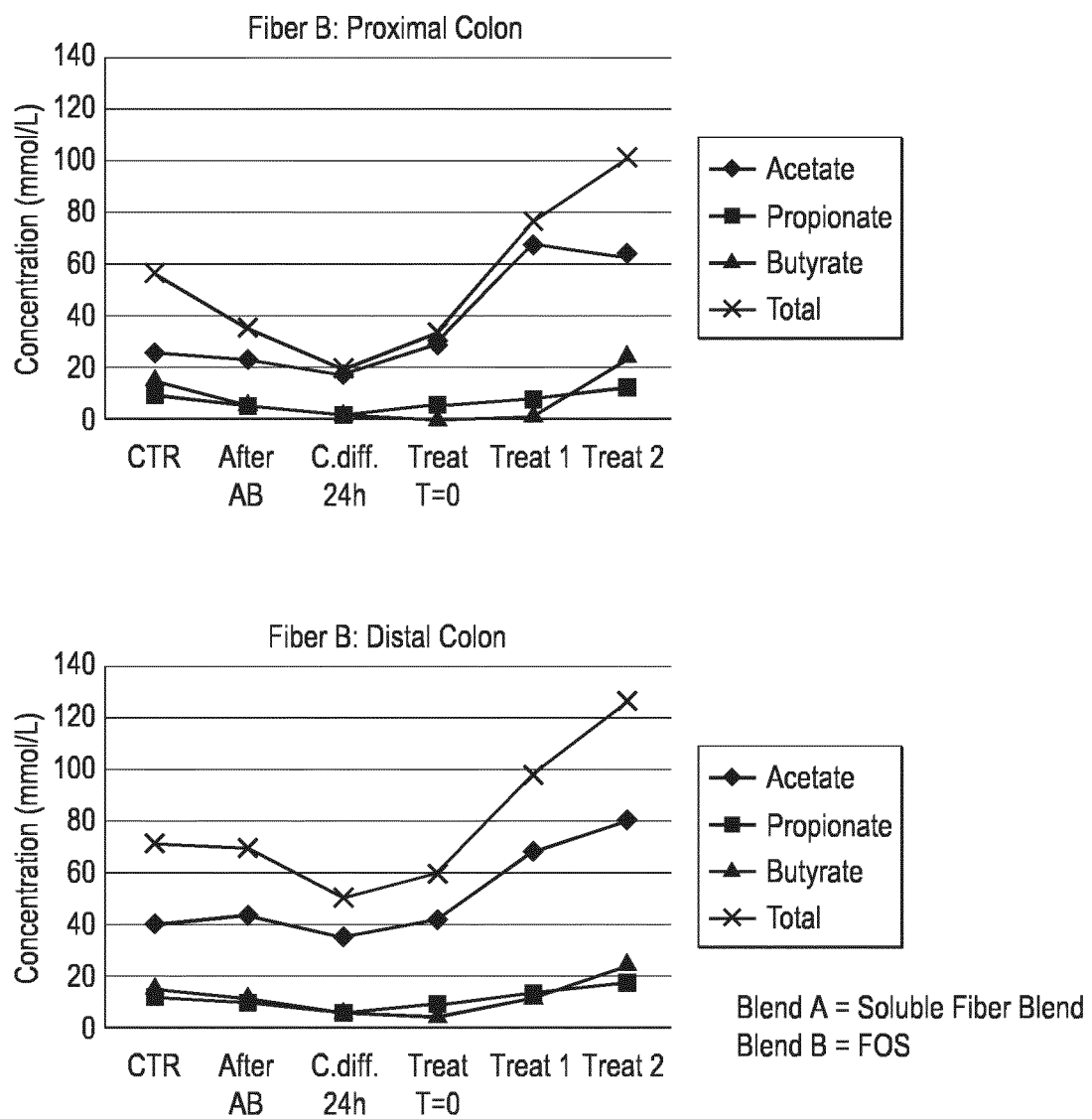
Figure 15:
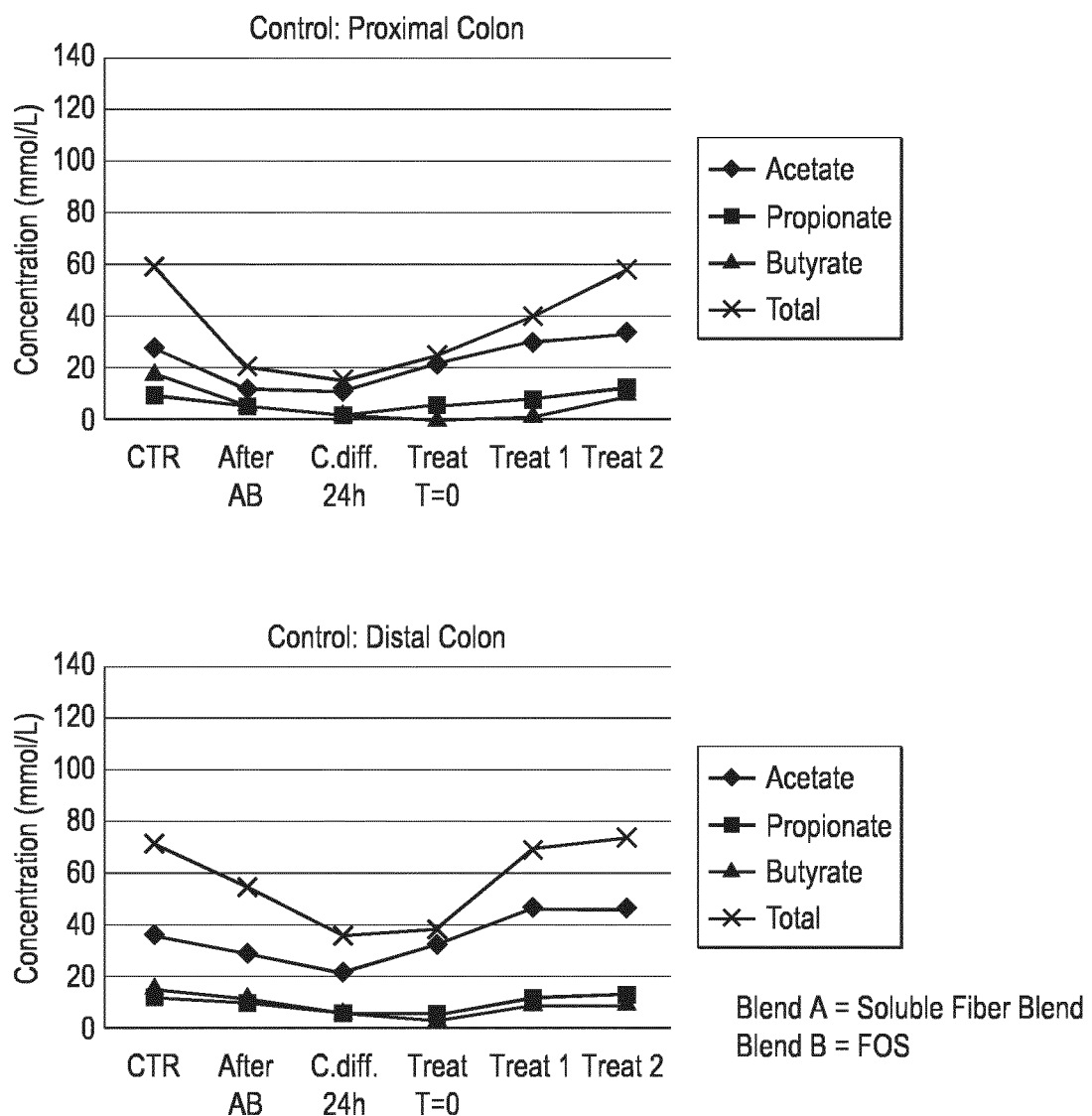

Samples were collected three times per week from all colon compartments to analyze the concentration of acetic acid, propionic acid, and butyric acid. In FIG. 15, the data are presented as total SCFA, acetate, propionate and butyrate production per experiment week of the SHIME experiment.

Both fiber treatments induced an increase in the total SCFA concentrations, which indicates that both products are well fermented in the gastrointestinal tract. SCFA production was disrupted by the antibiotic treatment and fiber treatments led to a quicker recovery of total SCFA production (FIG. 15). The final concentration of SCFA was higher when the fiber treatments were dosed to the SHIME as compared to the control, both in the proximal and distal colon vessels. In the distal colon, the Soluble Fiber Blend led to higher propionate than control.

Figure 16:
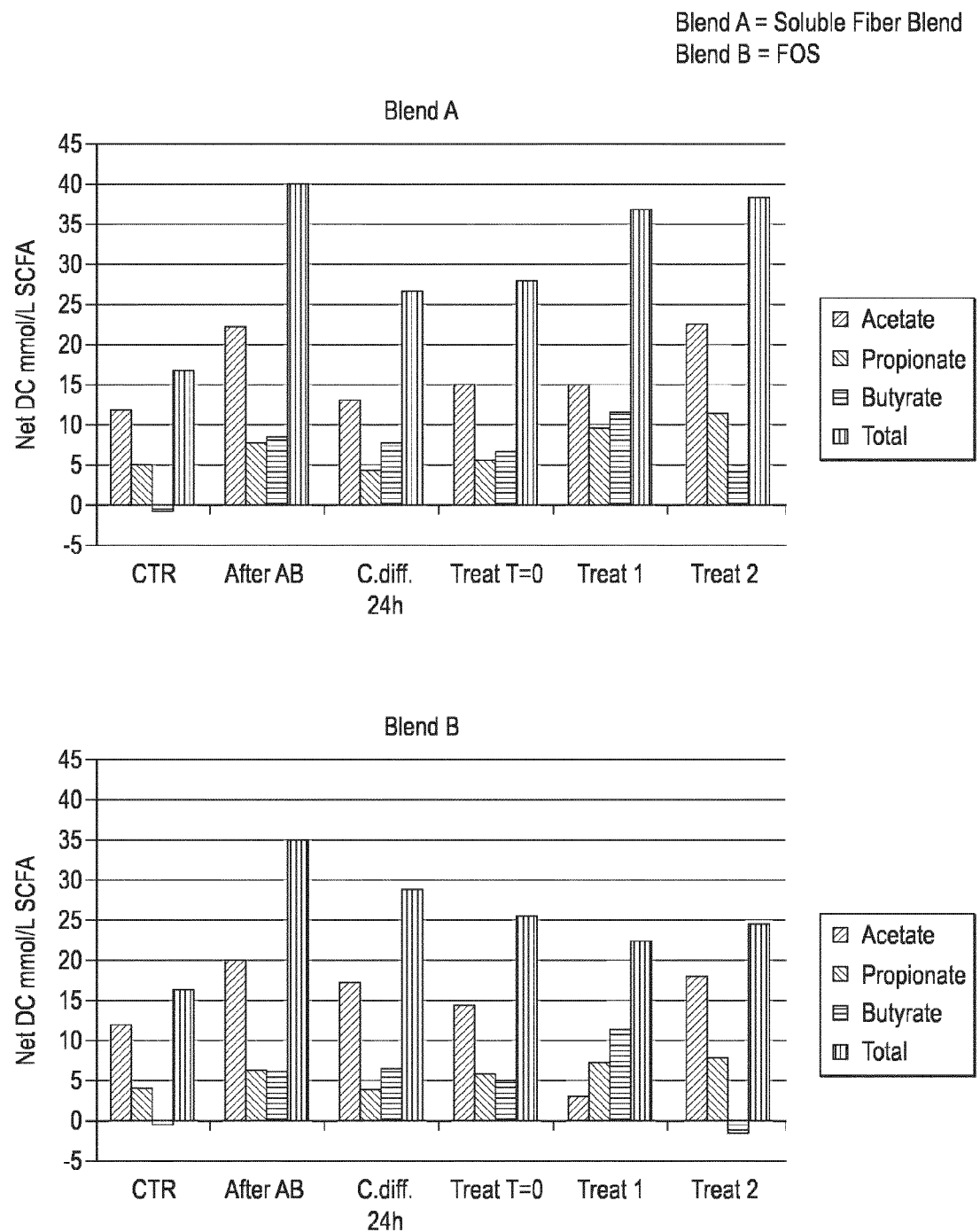
FIG. 16 shows bar chart representation of the net production of acetate, propionate, butyrate and total SCFA in the distal colon.

FIG. 16 shows the net production of acetate, propionate, butyrate and total SCFA in the distal colon to evaluate any possible difference in the main area of fermentation of the fiber treatments. The Soluble Fiber Blend led to a higher net production of all SCFA as compared to FOS. This indicates that FOS is fermented primarily in the proximal colon, while the Soluble Fiber Blend exhibits continued fermentation in the distal colon Results—pH Variation To ensure that optimal environmental conditions are maintained, the pH in a SHIME system is controlled by pH controllers in the following ranges: 5.6-5.9 (proximal colon); 6.5-6.8 (distal colon). Upon stabilization of the microbial community following the two week start-up period, acid-base consumption is normally low. However, during fiber treatment, the environment in the reactors may acidify due to production of SCFA, lactate, etc. This results in additional pH control by means of more administration of base to the respective reactors. In this context, the degree of acidification during the experiment can be used as a measure of the intensity of bacterial metabolism of the fiber blend.

Figure 17:
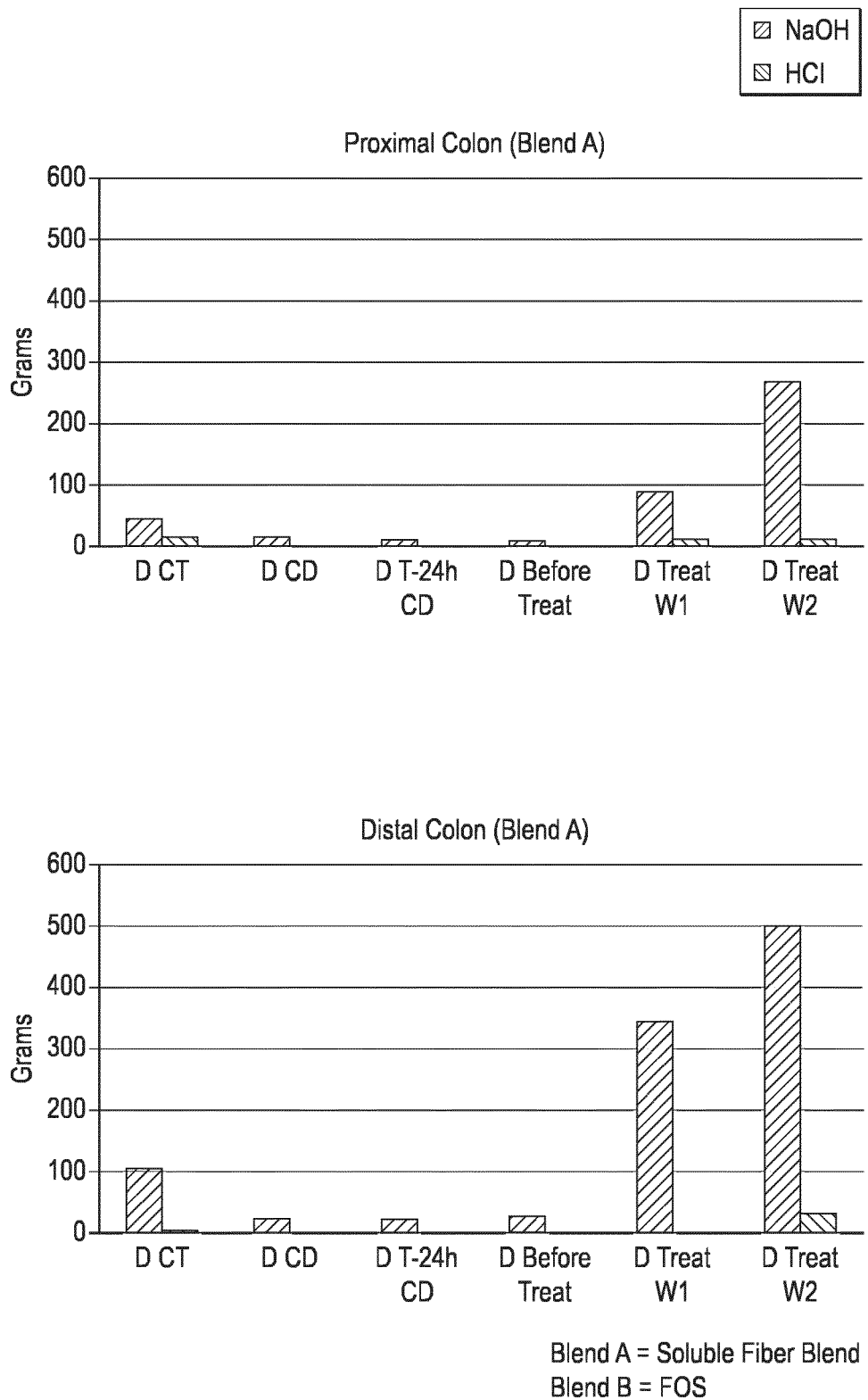
FIG. 17 shows bar chart representation of acid-base consumption per experimental period in the proximal and distal colon SHIME reactors.
Figure 17:
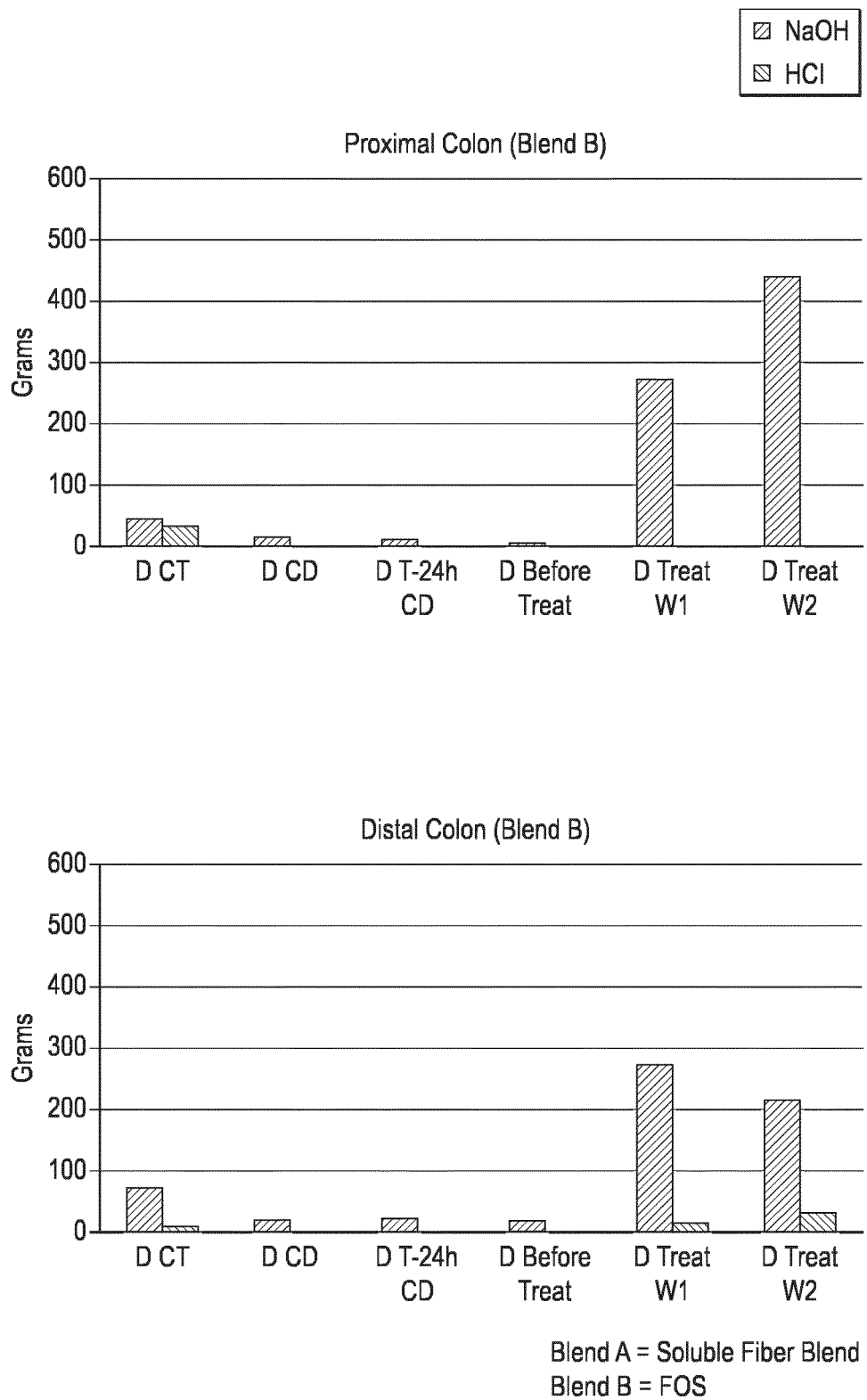
Figure 17:
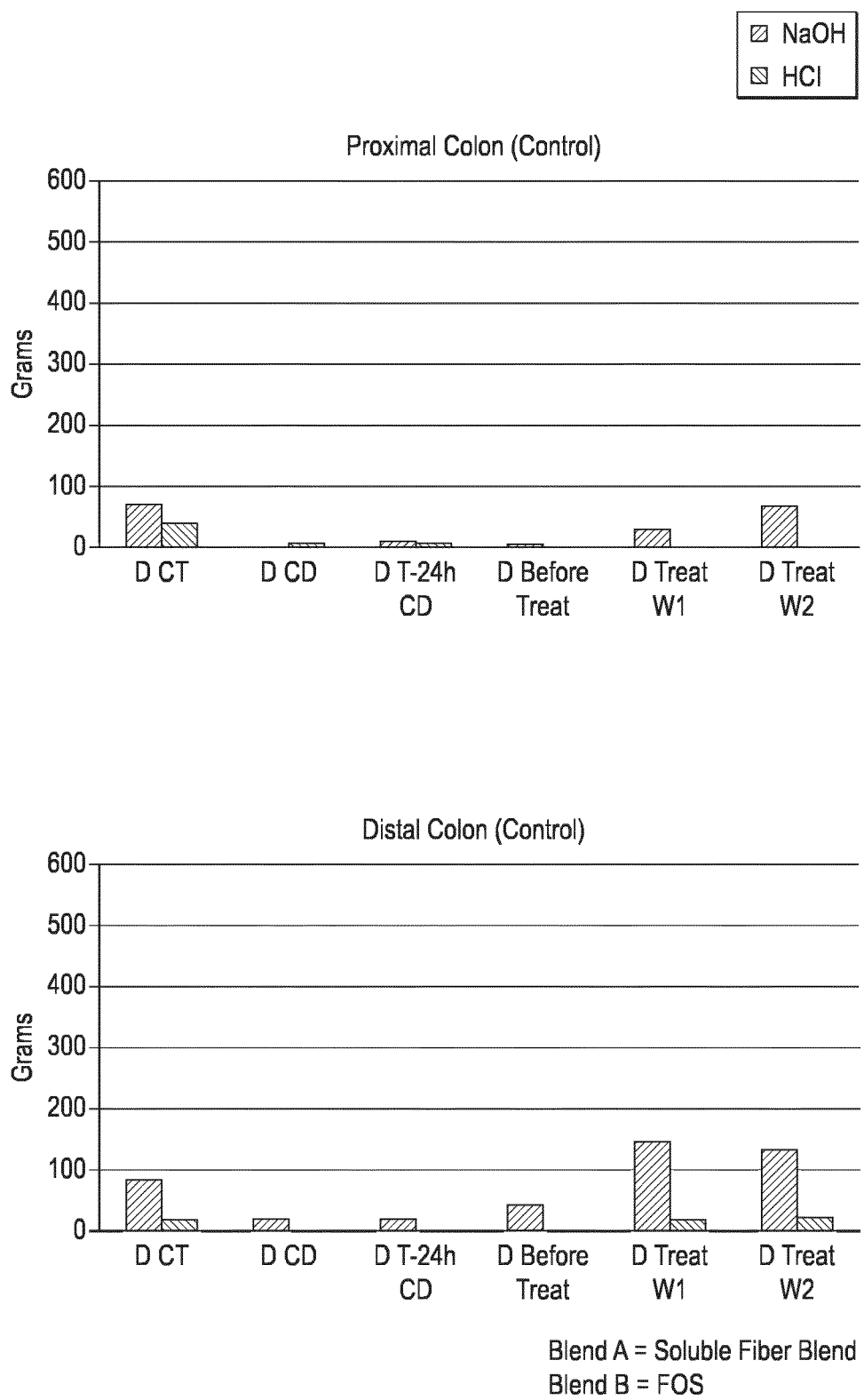

FIG. 17 shows acid-base consumption per experimental period. Administration of both blends induced acidification of the simulated colon reactors, indicative of an increased SCFA production and of a healthier intestinal environment. The Soluble Fiber Blend had a more gradual fermentation with a main acidification occurring in the distal colon; the main site of acidification for FOS was the proximal colon; the control diet led to a minimal acidification, indicating a good grade of stability of the microbiota.

Results—Microbial Community Composition

Samples were collected from the SHIME to evaluate the effect of the fiber treatments on the luminal microbial community composition by means of qPCR. Specifically, qPCR was used to monitor total bacteria, *Bifidobacteria*, and *Lactobacilli*.

Figure 18:
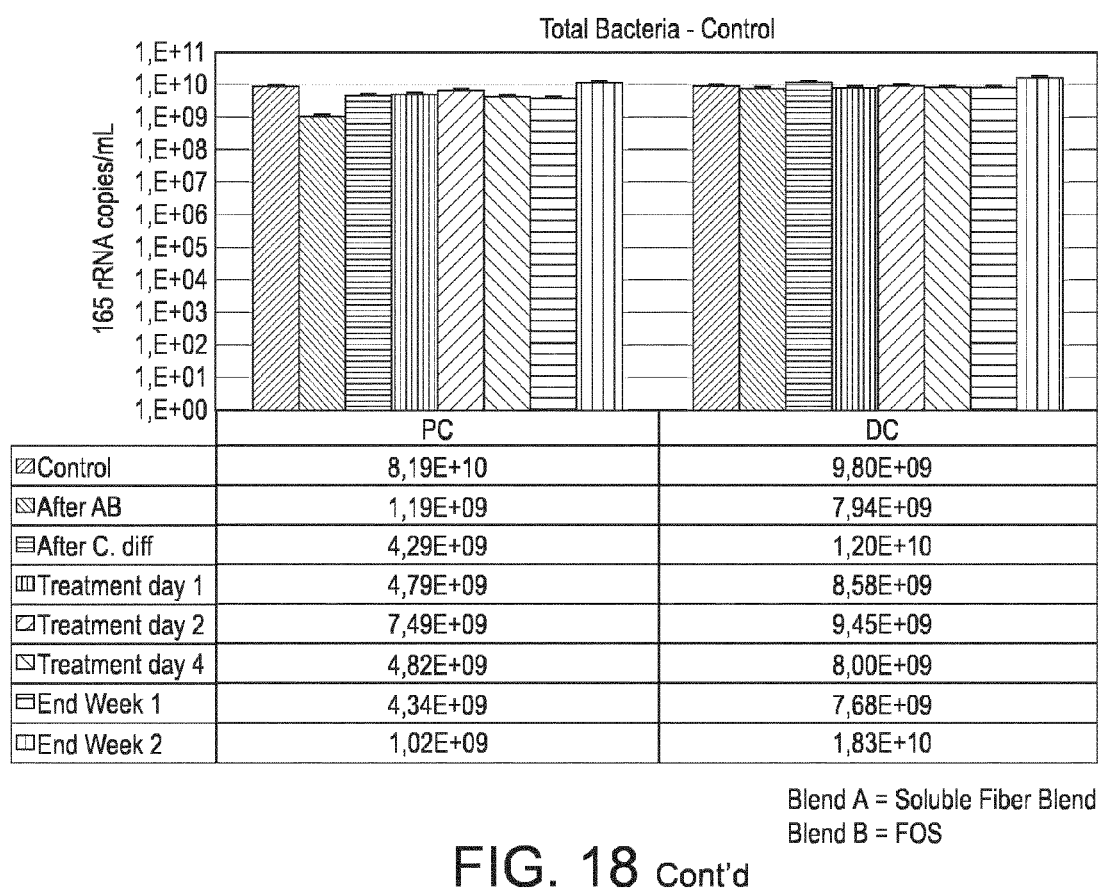
FIG. 18 shows qPCR data for the total bacteria concentration over the duration of the experiment for a control SHIME (starch), an SHIME with FOS as the fibre (Blend A) and a SHIME in which the fiber blend (Blend B) was used.

Antibiotic treatment led to a decrease in the concentration of total bacteria (FIG. 18). At the end of the experimental period, both fiber treatments led to a slightly higher concentration of total bacteria in both colon compartments as compared to the control SHIME.

Figure 19:
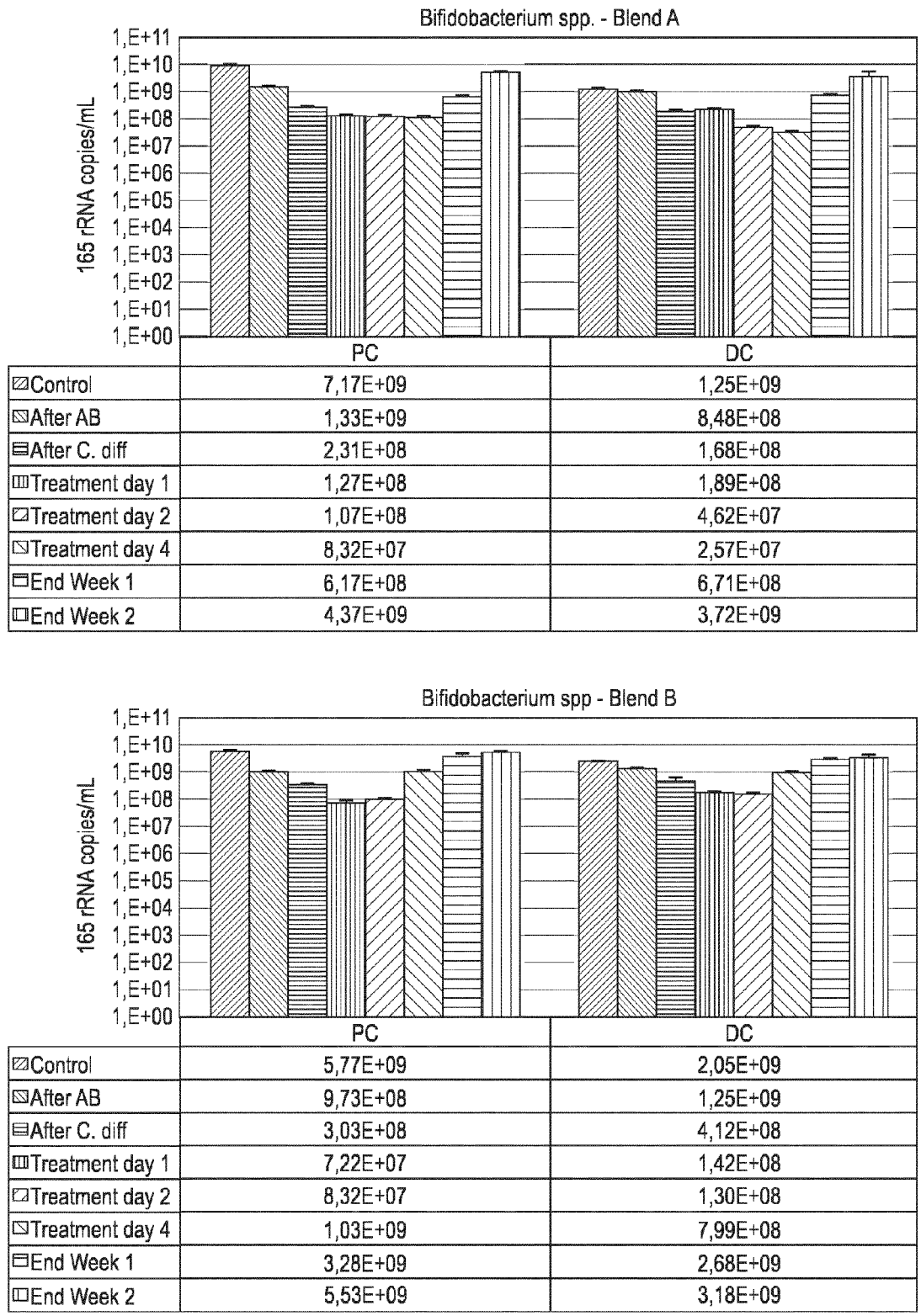
FIG. 19 shows qPCR data for the total *Bifidobacteria* over the duration of the experiment for a control SHIME (starch), an SHIME with FOS as the fibre (Blend A) and a SHIME in which the fiber blend (Blend B) was used.
Figure 19:
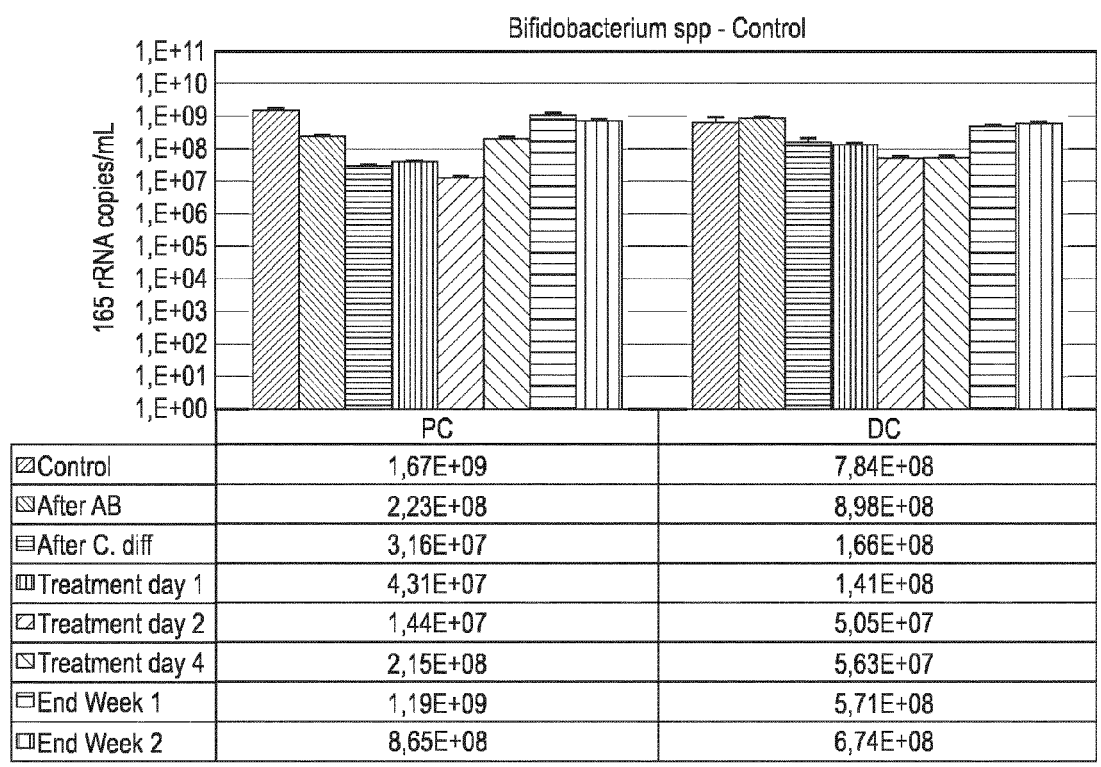

*Bifidobacteria* were affected by the antibiotic treatment and both fiber treatments led to a bifidogenic effect along the 2-week treatment period (FIG. 19). The final concentration of *Bifidobacteria* was higher (more than 0.5 log) at the end of the treatment as compared to the control SHIME in both colon compartments for both fiber treatments.

Figure 20:
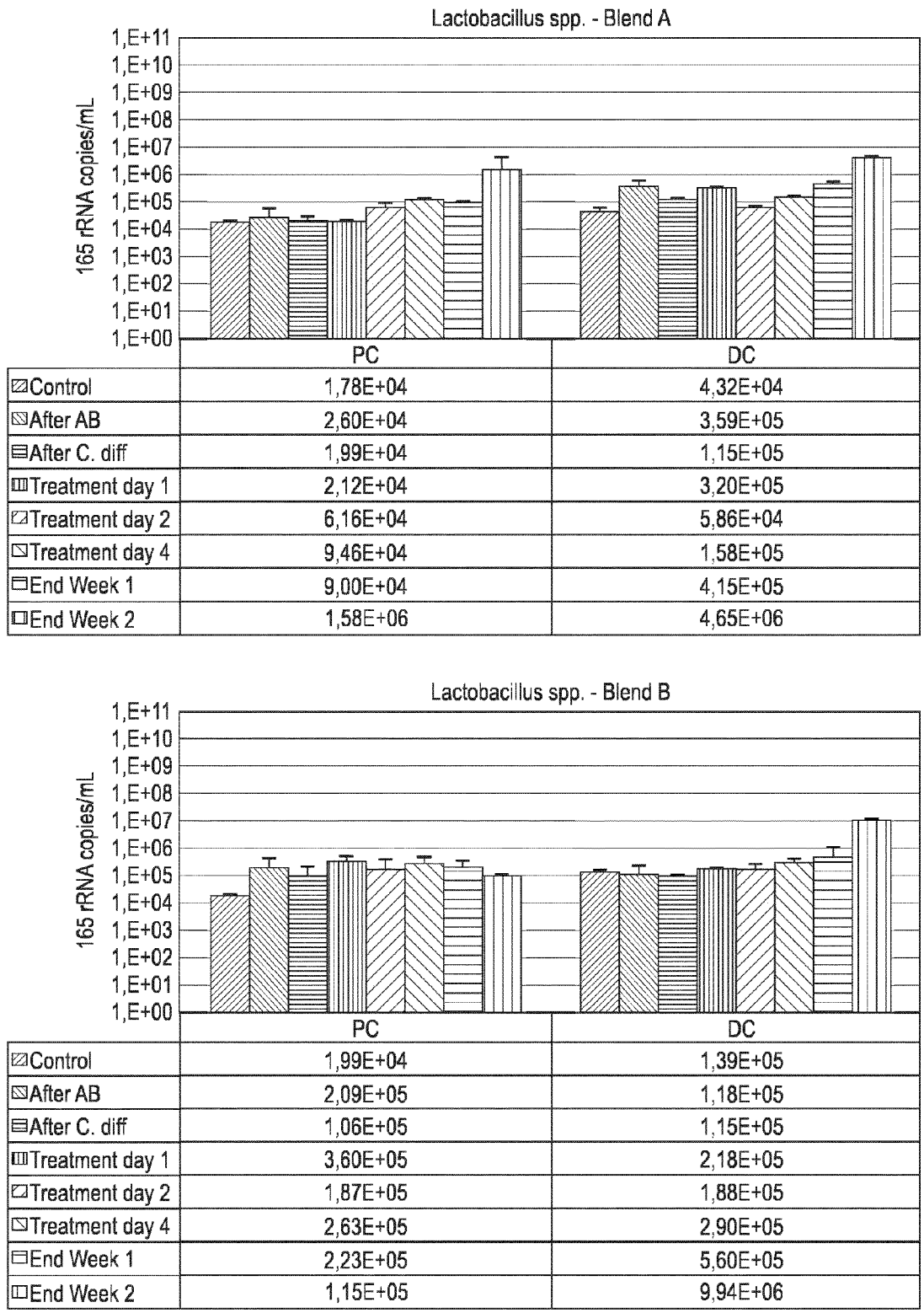
FIG. 20 shows shows qPCR data for the total *Lactobacilli* for each daily sample S1-S7 for a control SHIME (starch), an SHIME with FOS as the fibre (Blend A) and a SHIME in which the fiber blend (Blend B) was used.
Figure 20:
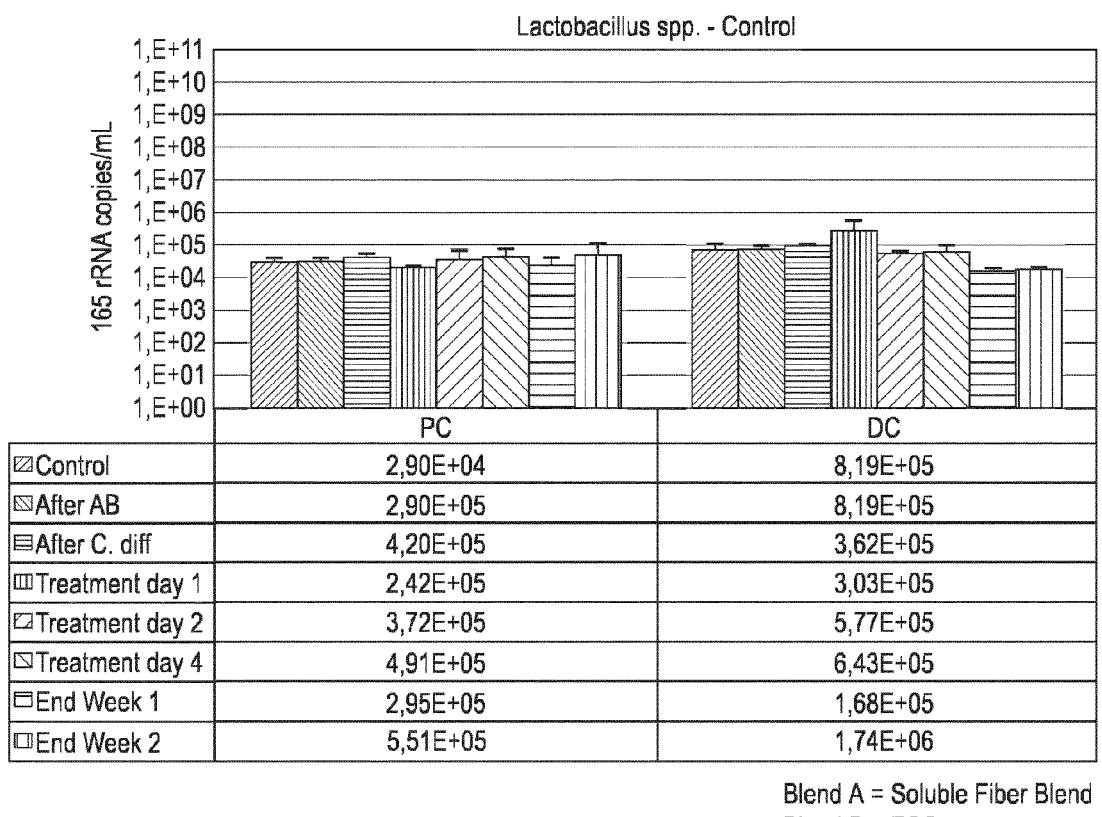

*Lactobacilli* appeared to be resistant to the antibiotic treatment. As compared to the control period, the Soluble Fiber Blend led to a lactobacillogenic effect in both colon compartments; FOS led to a positive effect only in the distal colon (FIG. 20).

Results—with Respect to Anti-pathogenic Activity

Figure 21:
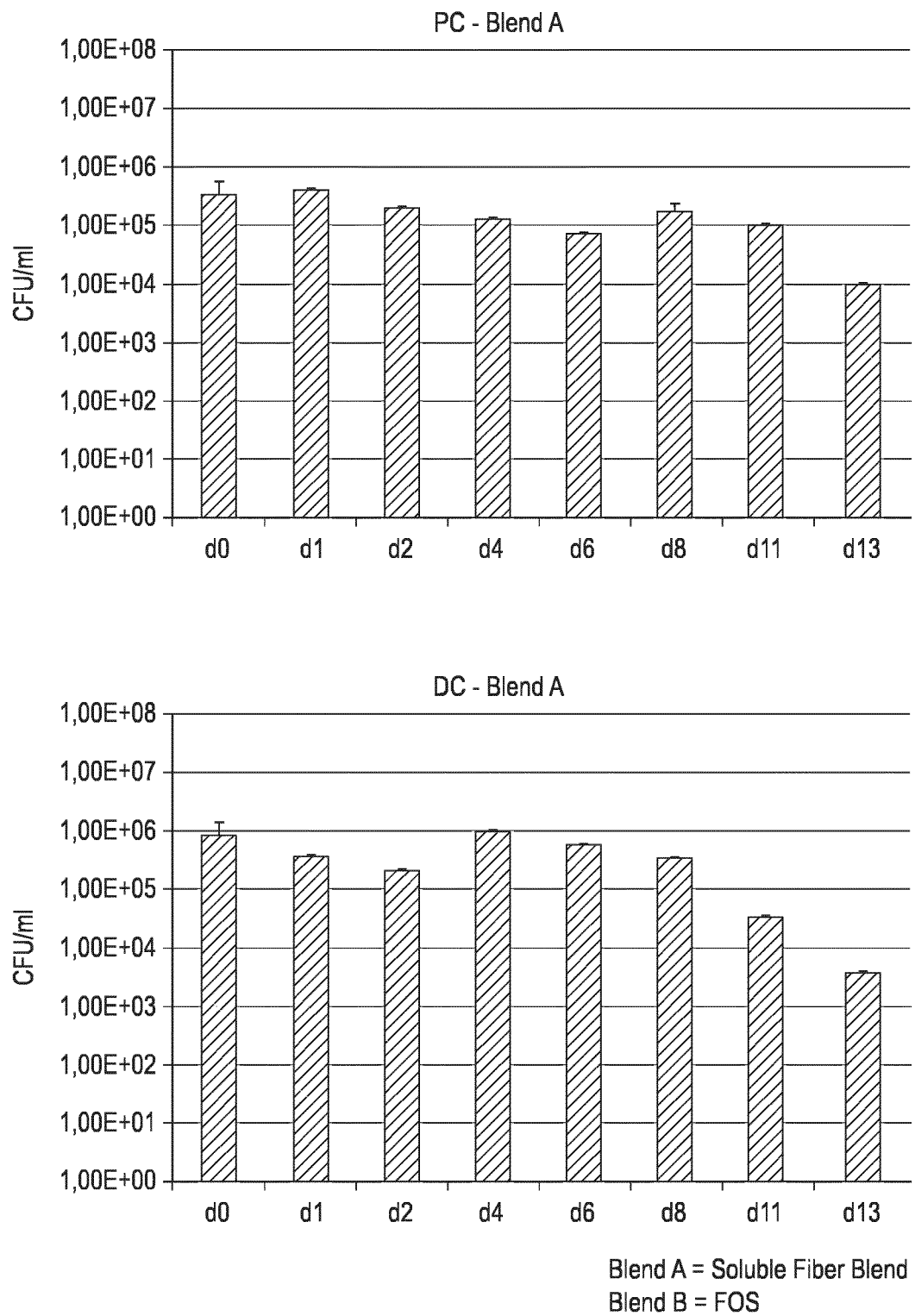
FIG. 21 shows plate count data for *C. difficile* in daily samples at day 0, day 1 day 2, day 4, day 6, day 8, day 11 and day 13 for a control SHIME (starch), an SHIME with FOS as the fibre (Blend A) and a SHIME in which the fiber blend (Blend B) was used.
Figure 21:
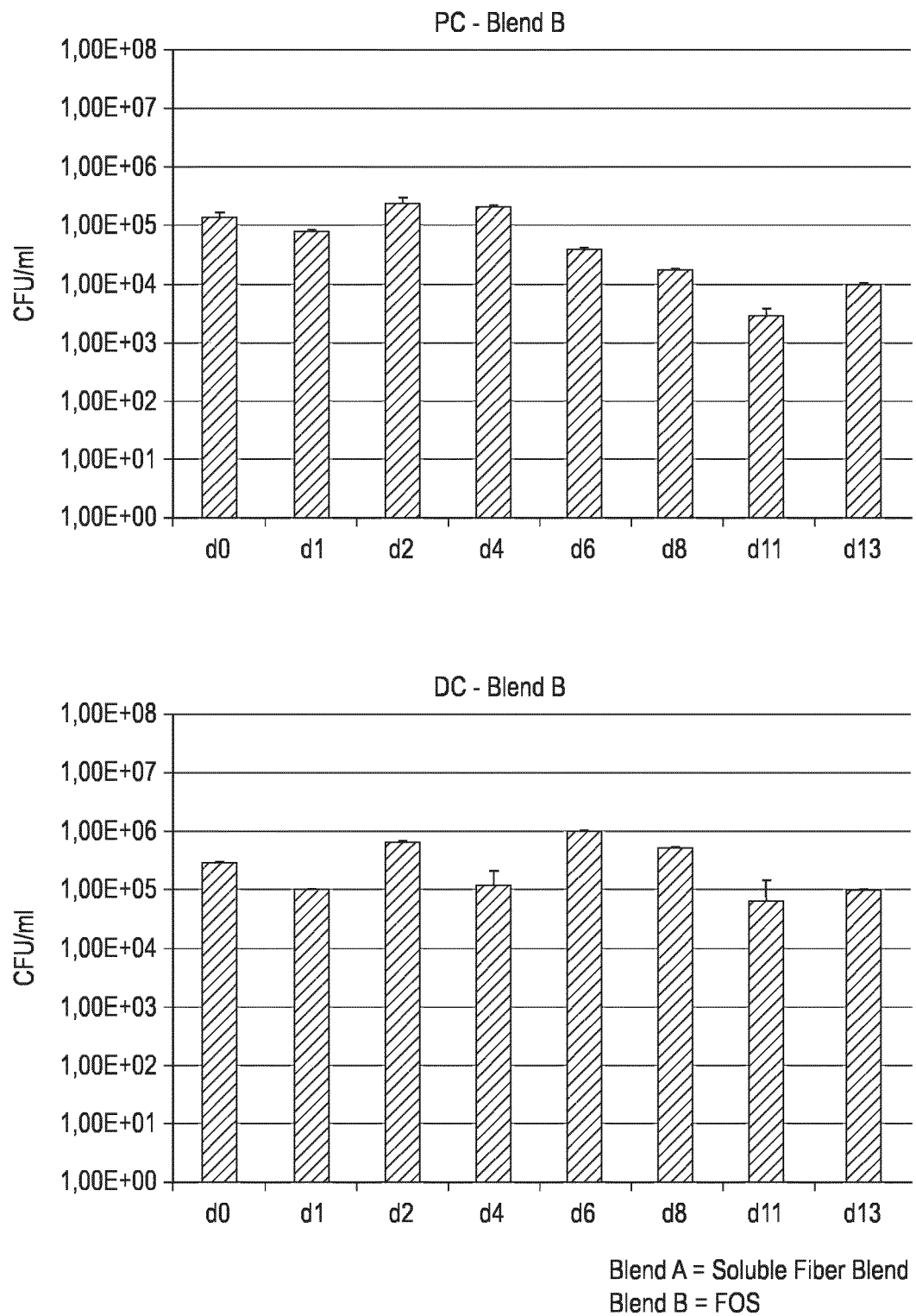
Figure 21:
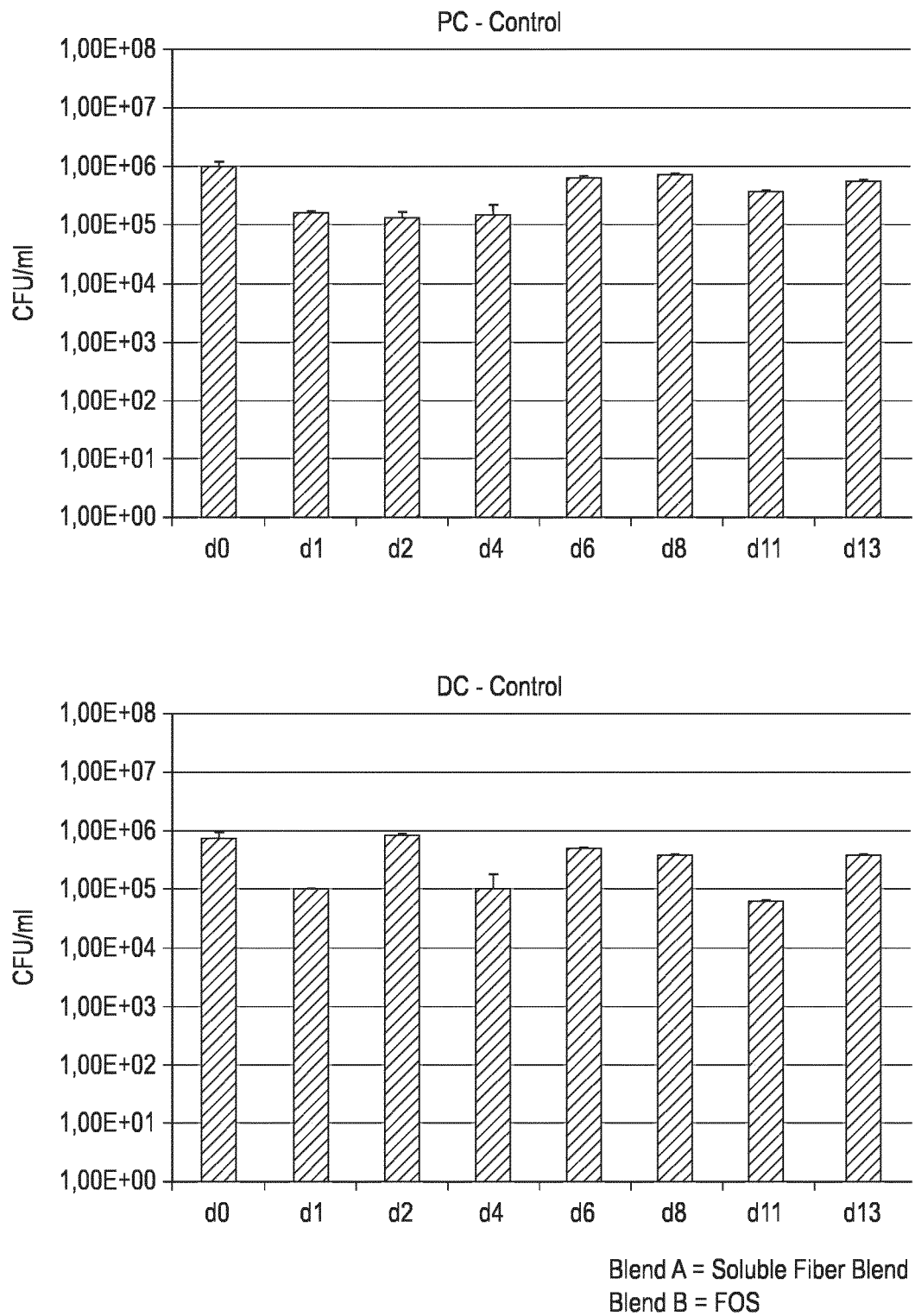

As compared to the control SHIME, plate counts showed that both fiber treatments led to a lower concentration of *C. difficile* in the proximal colon, starting from the second week of treatment ($p<0.05$). (FIG. 21). In the distal colon, the Soluble Fiber Blend led to a larger decrease (−2.5 log) in the concentration of viable *C. difficile* as compared to FOS, whose effect was less pronounced (approx. −0.5 log).

Figure 22:
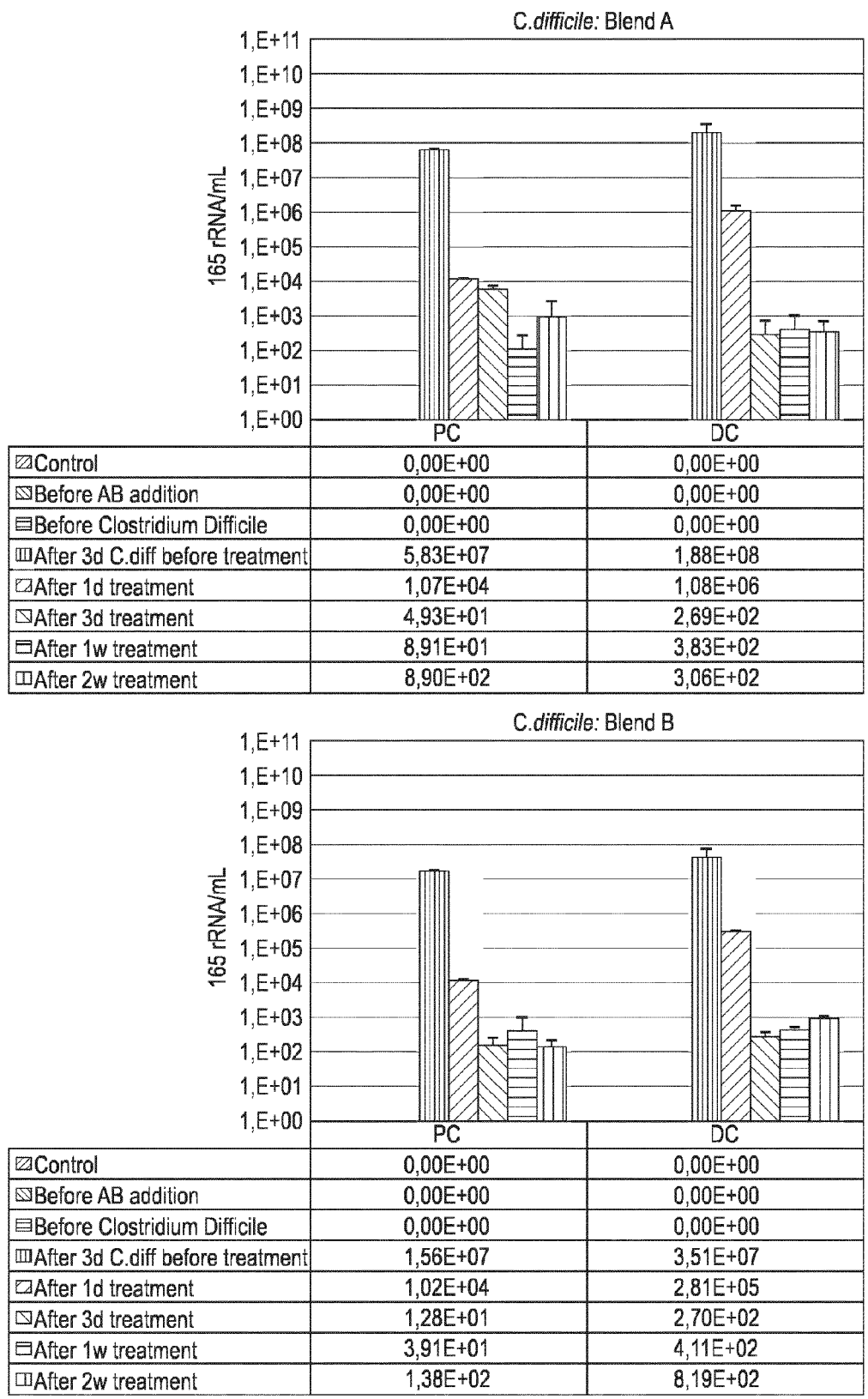
FIG. 22 shows qPCR data for *C. difficile* across the duration of the experiment for a control SHIME (starch), an SHIME with FOS as the fibre (Blend A) and a SHIME in which the fiber blend (Blend B) was used.
Figure 22:
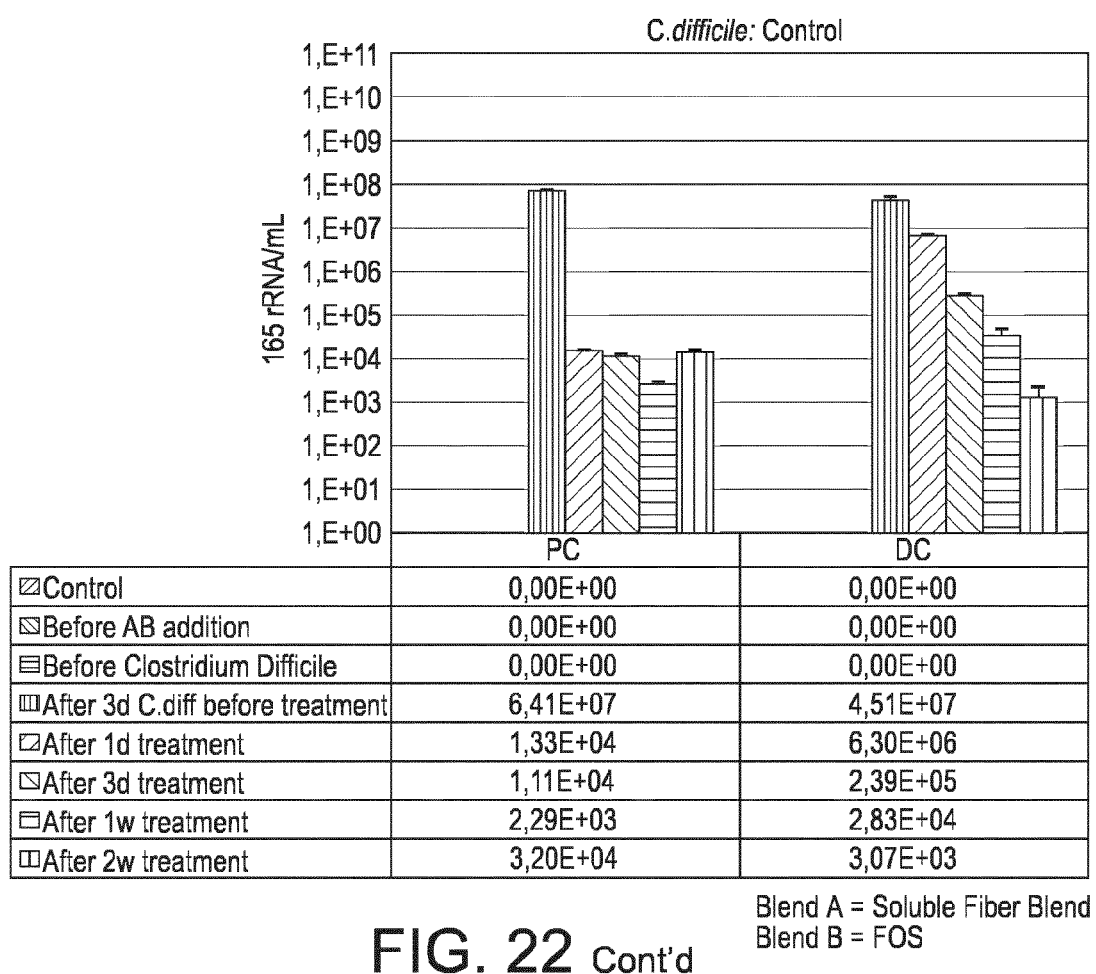

Plate counts provide information on the concentration of viable bacterial cells of the *C. difficile* strain. Conversely, qPCR allows quantification of the total amount of cells (i.e. both alive and dead). When observing the qPCR results (FIG. 22), both fiber treatments led to a lower concentration of the pathogen in both colon compartments. When compared to the control SHIME, both fiber treatments led to a lower concentration of *C. difficile* in the proximal colon (−1 log for the Soluble Fiber Blend and −2 log for FOS). In the distal colon, the final concentration was lower (−1 log) with the Soluble Fiber Blend as compared to the control SHIME.

It was not possible to detect any *C. difficile* cells adhering to the mucus. Most probably the antibiotic treatment did not open enough functional niches in the mucus layer in order to allow a successful competition of the pathogen with the autochthonous adhering microbiota.

An extra experiment was performed to evaluate the potential effect of the fiber treatments on toxin production. In this short-term experiment, *C. difficile* was grown in RCM medium in different penicillin flasks. After 24 hours, the concentration of toxins was measured and then the fiber treatments added. Five hours later the concentration of the toxins was measured again to assess the potential effect of the fiber treatments. Results are shown in table 1 below. The addition of FOS resulted in higher levels of toxin. As the Soluble Fiber Blend and Control showed a similar toxin production, the Soluble Fiber Blend does not seem to specifically adhere to/degrade the toxins.

TABLE 1

|  | T = 0 | 5 h |
| --- | --- | --- |
| Control | 0.178 | 0.636 |
| FOS | / | 1.143 |
| Soluble Fiber Blend | / | 0.69 |
| Neative Control | 0.048 | 0.05 |

In a parallel experiment, 10% of the main culture was used as inoculum for a new set of experiments in which the concentration of the toxins was measured during co-growth of the pathogen with the fiber treatments. The toxin level in presence of the Soluble Fiber Blend was lower as compared to control and FOS. This indicated a growth inhibiting effect of the Soluble Fiber Blend as compared to the other 2 conditions. Alternatively, it may also be possible that the strain grew without producing the toxins.

TABLE 2

|  | T = 0 | 24 h |
| --- | --- | --- |
| Control | 0.178 | 0.956 |
| FOS | / | 0.997 |
| Soluble Fiber Blend | / | 0.398 |
| Neative Control | 0.048 | 0.049 |

Various changes and modifications to the presently preferred embodiments described herein will be apparent to those skilled in the art. Such changes and modifications can be made without departing from the spirit and scope of the present subject matter and without diminishing its intended advantages. Such changes and modifications are covered by the appended claims.

The invention is claimed as follows:

1. A method comprising the steps of:
    administering to a patient that has received an antibiotic treatment and has a *C. difficile* infection, a therapeutically effective amount of a fiber blend comprising fructo-oligosaccharides (FOS), acacia gum and inulin to treat the *C. difficile* infection, after the antibiotic treatment.

2. The method of claim 1, wherein the fiber blend further comprises at least one insoluble fiber, wherein the at least one insoluble fiber is selected from the group consisting of a soy fiber, an outer pea fiber and combinations thereof.

3. The method of claim 1, wherein the fiber blend further comprises outer pea fibers.

4. A method comprising the steps of:
    administering to a patient that has received an antibiotic treatment and has a *C. difficile* infection a nutritional composition after the antibiotic treatment, the composition containing a therapeutically effective amount of a fiber blend comprising fructo-oligosaccharides (FOS), acacia gum and inulin to treat the *C. difficile* infection.

5. The method of claim 4, wherein the fiber blend further comprises outer pea fibers, wherein the FOS, the acacia gum, the inulin and the outer pea fibers are the only fibers in the nutritional composition.

6. The method of claim 4, wherein the fiber blend further comprises at least one insoluble fiber, wherein the at least one insoluble fiber is selected from the group consisting of a soy fiber, an outer pea fiber and combinations thereof.

7. The method of claim 4, wherein the nutritional composition is administered enterally.

8. The method of claim 4, wherein the composition is administered orally.

9. The method of claim 4, wherein the nutritional composition is administered to the patient at least daily for at least one week after the antibiotic treatment.

10. The method of claim 9, wherein probiotics are not administered to the patient during the at least one week.

11. The method of claim 9, wherein the patient does not receive another antibiotic treatment during the at least one week.

12. A method comprising the steps of:
administering to a patient that has received an antibiotic treatment and has a *C. difficile* infection a nutritional composition at least daily for at least one week after the antibiotic treatment, the composition containing a therapeutically effective amount of a fiber blend comprising fructo-oligosaccharides (FOS), acacia gum and inulin to treat the *C. difficile* infection.

13. A method comprising the steps of:
administering to a patient that will receive an antibiotic treatment a nutritional composition, at least daily for at least one week before the antibiotic treatment, the composition containing a therapeutically effective amount of a fiber blend comprising fructo-oligosaccharides (FOS), acacia gum and inulin to treat a *C. difficile* infection.

14. A method comprising the steps of:
administering to a patient that has received an antibiotic treatment and has a *C. difficile* infection a nutritional composition after the antibiotic treatment, the composition containing a therapeutically effective amount of a fiber blend comprising fructo-oligosaccharides (FOS), acacia gum, inulin and outer pea fibers to treat the *C. difficile* infection.

15. A method comprising the steps of:
administering to a patient that has received an antibiotic treatment and has a *C. difficile* infection a nutritional composition, after the antibiotic treatment, the composition containing a therapeutically effective amount of a fiber blend comprising fructo-oligosaccharides (FOS), acacia gum and inulin to improve recovery of *Lactobacilli* concentration.

16. A method comprising the steps of:
administering to a patient that has received an antibiotic treatment and has a *C. difficile* infection a nutritional composition, after the antibiotic treatment, the composition containing a therapeutically effective amount of a fiber blend comprising fructo-oligosaccharides (FOS), acacia gum and inulin to improve recovery of production of short chain fatty acids.

17. A method comprising the steps of:
administering to a patient that has received an antibiotic treatment and has a *C. difficile* infection a nutritional composition, after the antibiotic treatment, the composition containing a therapeutically effective amount of a fiber blend comprising fructo-oligosaccharides (FOS), acacia gum and inulin to improve recovery of lactate production.

18. A method comprising the steps of:
administering to a patient that has received an antibiotic treatment and has a *C. difficile* infection a nutritional composition, after the antibiotic treatment, the composition containing a therapeutically effective amount of a fiber blend comprising fructo-oligosaccharides (FOS), acacia gum and inulin to improve recovery of *Bifidobacteria* concentration.

19. A method comprising the steps of:
administering to a patient that has received an antibiotic treatment and has a *C. difficile* infection a nutritional composition, after the antibiotic treatment, the composition containing a therapeutically effective amount of a fiber blend comprising fructo-oligosaccharides (FOS), acacia gum and inulin to improve recovery of Bacteriodetes concentration.

20. A method comprising the steps of:
administering to a patient that has received an antibiotic treatment and has a *C. difficile* infection a nutritional composition, after the antibiotic treatment, the composition containing a therapeutically effective amount of a fiber blend comprising fructo-oligosaccharides (FOS), acacia gum and inulin to improve recovery of Firmicutes concentration.

21. A method comprising the steps of:
administering to a patient that has received an antibiotic treatment and has a *C. difficile* infection a nutritional composition, after the antibiotic treatment, the composition containing a therapeutically effective amount of a fiber blend comprising fructo-oligosaccharides (FOS), acacia gum and inulin to improve recovery of total bacteria concentration.

22. A method comprising the steps of:
administering to a patient that has received an antibiotic treatment and has a *C. difficile* infection a nutritional composition, after the antibiotic treatment, the composition containing a therapeutically effective amount of a fiber blend comprising fructo-oligosaccharides (FOS), acacia gum and inulin to improve colonic acidification.

23. A method comprising the steps of:
administering to a patient that has received an antibiotic treatment and has a *C. difficile* infection a nutritional composition, after the antibiotic treatment, the composition containing a therapeutically effective amount of a fiber blend comprising fructo-oligosaccharides (FOS), acacia gum and inulin to reduce toxin levels in the colon.

24. The method of claim 1, wherein the fiber blend comprises FOS in an amount of about 35 to about 44% by weight; acacia gum in an amount of about 38% to about 50% by weight; and inulin in an amount of 12 to 24% by weight.

25. The method of claim 1, wherein the fiber blend further comprises partially hydrolyzed guar gum (PHGG).

26. The method of claim 1, wherein the fiber blend comprises soluble fibers and insoluble fibers, wherein the soluble fiber and insoluble fiber are present in a ratio of between about 60:40 to about 40:60.

27. The method of claim 4, wherein the fiber blend comprises FOS in an amount of about 35 to about 44% by weight; acacia gum in an amount of about 38% to about 50% by weight; and inulin in an amount of 12 to 24% by weight.

28. The method of claim 4, wherein the fiber blend further comprises partially hydrolyzed guar gum (PHGG).

29. The method of claim 4, wherein the fiber blend comprises soluble fibers and insoluble fibers, wherein the soluble fiber and insoluble fiber are present in a ratio of between about 60:40 to about 40:60.

30. The method of claim 12, wherein the fiber blend comprises FOS in an amount of about 35 to about 44% by weight; acacia gum in an amount of about 38% to about 50% by weight; and inulin in an amount of 12 to 24% by weight.

31. The method of claim 12, wherein the fiber blend further comprises partially hydrolyzed guar gum (PHGG).

32. The method of claim 12, wherein the fiber blend comprises soluble fibers and insoluble fibers, wherein the soluble fiber and insoluble fiber are present in a ratio of between about 60:40 to about 40:60.

33. he method of claim 13, wherein the fiber blend comprises FOS in an amount of about 35 to about 44% by weight; acacia gum in an amount of about 38% to about 50% by weight; and inulin in an amount of 12 to 24% by weight.

34. The method of claim 13, wherein the fiber blend further comprises partially hydrolyzed guar gum (PHGG).

35. The method of claim 13, wherein the fiber blend comprises soluble fibers and insoluble fibers, wherein the soluble fiber and insoluble fiber are present in a ratio of between about 60:40 to about 40:60.

* * * * *